United States Patent
Clark et al.

(10) Patent No.: US 9,382,339 B2
(45) Date of Patent: Jul. 5, 2016

(54) MICROWAVE ASSISTED CITRUS WASTE BIOREFINERY

(71) Applicant: University of York, York (GB)

(72) Inventors: James Hanley Clark, York (GB); Lucie Anne Pfaltzgraff, York (GB); Vitaliy Lvovich Budarin, York (GB); Mario De Bruyn, York (GB)

(73) Assignee: University of York, Heslington (GB)

( * ) Notice: Subject to any disclaimer, the term of this patent is extended or adjusted under 35 U.S.C. 154(b) by 0 days.

(21) Appl. No.: 14/390,633

(22) PCT Filed: Apr. 4, 2013

(86) PCT No.: PCT/GB2013/000154
§ 371 (c)(1),
(2) Date: Oct. 3, 2014

(87) PCT Pub. No.: WO2013/150262
PCT Pub. Date: Oct. 10, 2013

(65) Prior Publication Data
US 2015/0065698 A1    Mar. 5, 2015

(30) Foreign Application Priority Data
Apr. 4, 2012 (GB) .................................. 1206034.9

(51) Int. Cl.
| | | |
|---|---|---|
| C07C 29/76 | (2006.01) |
| C07C 7/10 | (2006.01) |
| C07D 307/50 | (2006.01) |
| C07H 1/08 | (2006.01) |
| C08B 1/00 | (2006.01) |
| C08B 37/00 | (2006.01) |
| B01J 19/12 | (2006.01) |
| C07C 13/21 | (2006.01) |
| C07C 33/14 | (2006.01) |
| C07D 307/48 | (2006.01) |
| C07D 311/60 | (2006.01) |
| C07H 3/02 | (2006.01) |

(52) U.S. Cl.
CPC .............. *C08B 37/0045* (2013.01); *C07C 7/10* (2013.01); *C07C 13/21* (2013.01); *C07C 29/76* (2013.01); *C07C 33/14* (2013.01); *C07D 307/48* (2013.01); *C07D 307/50* (2013.01); *C07D 311/60* (2013.01); *C07H 1/08* (2013.01); *C07H 3/02* (2013.01); *C08B 1/00* (2013.01); *C08B 37/0048* (2013.01); *C07C 2101/16* (2013.01)

(58) Field of Classification Search
None
See application file for complete search history.

(56) References Cited

U.S. PATENT DOCUMENTS

| | | |
|---|---|---|
| 4,497,838 A | 2/1985 | Bonnell |
| 6,143,337 A | 11/2000 | Fishman et al. |
| 7,060,313 B2 | 6/2006 | Jones |
| 2006/0204624 A1 | 9/2006 | Patist et al. |

FOREIGN PATENT DOCUMENTS

WO    2006/096884    9/2006

OTHER PUBLICATIONS

CN 1749379 A, Mar. 22, 2006, machine translation.*
Bagherian et al., Comparisons between conventional, microwave- and ultrasound-assisted methods for extraction of pectin from grapefruit, Chemical Engineering and Processing, 50:1237-1243, 2011.
Bampidis et al., "Citrus by-products as ruminant feeds: A review," Animal Feed Science and Technology, 128:175-217, 2006.
Bevill, "Freshly Squeezed Ethanol Feedstock," Biomassmaginze.com/articles/1531-squeezed-ethanol-feedstock, Jan. 14, 2016, 2 pgs.
Bousbia et al., A new process for extraction of essential oil from Citrus peels: Microwave hydrodiffusion and gravity, Journal of Food Engineering, 90:409-413, 2009.
Braddock, "Chapter 12 d-Limonene," Handbook of Citrus By-Products and Processing Technology, John Wiley & Sons, Inc., pp. 175-189, 1999.
Budarin et al., "Use of green chemical technologies in an integrated biorefinery," Energy & Environmental Science, 4:471-479, 2011.
Citrus clementina, http://www.cns.fr/spip/Citrus-clementina-Mediterranean.html, Jan. 14, 2016, 1 pg.
Clark et al., "Microwave Processing of Materials," Annu Rev. Mater. Sci, 26:299-331, 1996.
De La Hoz et al., "Microwaves in organic synthesis. Thermal and non-thermal microwave effects," Chem. Soc. Rev., 34:164-178, 2005.
Donaghy et al., "Pectin Extraction from Citrus Peel by Polygalacturonase Produced on Whey," Bioresource Technology 47:25-28 (1994).
Farhat et al., "Microwave steam diffusion for extraction of essential oil from orange peel: Kinetic data, extract's global yield and mechanism," Food Chemistry, 125:255-261, 2011.
Ferhat et al., "An improved microwave Clevenger apparatus for distillation of essential oils from orange peel," Journal of Chromatography A, 1112:121-126, 2006.
Ferreira-Leitão et al., "Biomass Residues in Brazil. Availability and Potential Uses," Waste Biomass Valor 1:65-76, 2010.
Fishman et al., "Characterization of pectin, flash-extracted from orange albedo by microwave heating, under pressure," Carbohydrate Research, 323:126-138, 2000.
Fishman et al., "Microwave-assisted extraction of lime pectin," Food Hydrocolloids, 20:1170-1177, 2006.
Food Chemicals Codex, National Research Council, 3$^{rd}$ Edition, National Academy Press, pp. 215-217, 1981.
Gronnow et al., "Energy Efficiency in Chemical Reactions: A Comparative Study of Different Reaction Techniques," Organic Process Research & Development, 9:516-518, 2005.

(Continued)

*Primary Examiner* — Layla Berry
(74) *Attorney, Agent, or Firm* — K&L Gates LLP

(57) ABSTRACT

There is described a method of isolating one or more of pectin, d-limonene, a flavor compound, a flavonoid, a soluble monosaccharide, a decomposition product of a monosaccharide and cellulose, from citrus material wherein said method comprises the microwave assisted hydrothermal low temperature treatment of citrus material.

18 Claims, 17 Drawing Sheets

(56) References Cited

OTHER PUBLICATIONS

Guolin et al., "Application of Ionic Liquids in the Microwave-Assisted Extraction of Pectin from Lemon Peels," Journal of Analytical Methods in Chemistry, 6(3):13-18, 2012.
Hayat et al., "Liberation and separation of phenolic compounds from citrus mandarin peels by microwave heating and its effect on antioxidant activity," Separation and Purification Technology 73:371-376, 2010.
Hayat et al., "Effect of microwave treatment on phenolic content and antioxidant activity of citrus mandarin pomace," Food Chemistry, 123:423-429, 2010.
Inoue et al., "Isolation of hesperidin from peels of thinned Citrus unshiu fruits by microwave-assisted extraction," Food Chemistry 123:542-547, 2010.
Kalra et al., "Bioconversion of kinnow-mandarin waste into single-cell protein," MIRCEN Journal, 5:321-326, 1989.
Kappe, "Controlled Microwave Heating in Modern Organic Synthesis," Angew. Chem. Int. Ed., 43:6250-6284, 2004.
Kimball, "Citrus Processing, A Complete Guide," Aspen Publishers, pp. 354-355, 1999.
Kratchanova et al., "The effect of microwave heating of fresh orange peels on the fruit tissue and quality of extracted pectin," Carbohydrate Polymers 56:181-185, 2004.
Kratchanova et al., "Influence of microwave pretreatment of fresh orange peels on pectin extraction," Pectins and Pectinases, 14:941-946, 1996.
Kroyer, "Impact of Food Processing on the Environment—an Overview," Lebensm.-Wiss. U.-Technol., 28:547-552, 1995.
Kumar et al., "Extraction and characterization of pectin from apple pomace and its evaluation as lipase (steapsin) inhibitor," Carbohydrate Polymers, 82:454-459, 2010.
Li et al., "Succinic acid production from orange peel and wheat straw by batch fermentations of *Fibrobacter succinogenes* S85," Appl Microbiol Biotechnol, 88:671-678, 2010.
Liu et al., "Water-based extraction of pectin from flavedo and albedo of orange peels," Chemical Engineering Journal 120:203-209, 2006.
López et al., "Biorefinery of waste orange peel," Critical Reviews in Biotechnology, 30(1):63-69, 2010.
Ma et al., "Integrated Utilization of Orange Peel," Bioresource Technology, 44:61-63, 1993.
Mamma et al., "Chapter 14—Biotechnological Potential of Fruit Processing Industry Residues," Biotechnology for Agro-Industrial Residues, P. Sing nee' Nigam and A. Pandey, eds., Springer Science + Business Media B.V. 2009, pp. 273-275.
Marín et al., "By-products from different citrus processes as a source of customized functional fibres," Food Chemistry 100:736-741, 2007.
Özmen et al., "Biogas production from municipal waste mixed with different portions of orange peel," University of Borås School of Engineering, 2009, 39 pgs.
Sahraoui et al., "Valorization of citrus by-products using Microwave Steam Distillation (MSD)," Innovative Food Science and Emerging Technologies, 12:163-170, 2011.
Steinbüchel et al. editors, Polysaccharides and Polyamides in the Food Industry, vol. 1, 10 Pectins, Wiley-VCH, 2005, pp. 351-381.
White et al., "Pectin-Derived Porous Materials," European Journal of Chemistry, 16:1326-1335, 2010.
Widmer et al., "Pretreatment effects on orange processing waste for making ethanol by simultaneous saccharification and fermentation," Bioresource Technology 101:5242-5249, 2010.
Yu et al., "Physical and Chemical Properties of Bio-Oils From Microwave Pyrolysis of Corn Stover," Applied Biochemistry and Biotechnology, vol. 136-140, pp. 950-957, 2007.
Zhongdong et al., "Image study of pectin extraction from orange skin assisted by microwave," Carbohydrate Polymers 64:548-552, 2006.
Zhou, "Developments in Ethanol Production from Citrus Peel Waste," Proc. Fla. State Hort. Soc., 121:307-310, 2008.

\* cited by examiner

Scheme of processing of orange peel based on microwave hydrothermal pyrolysis. E.A. corresponds to ethyl-acetate.

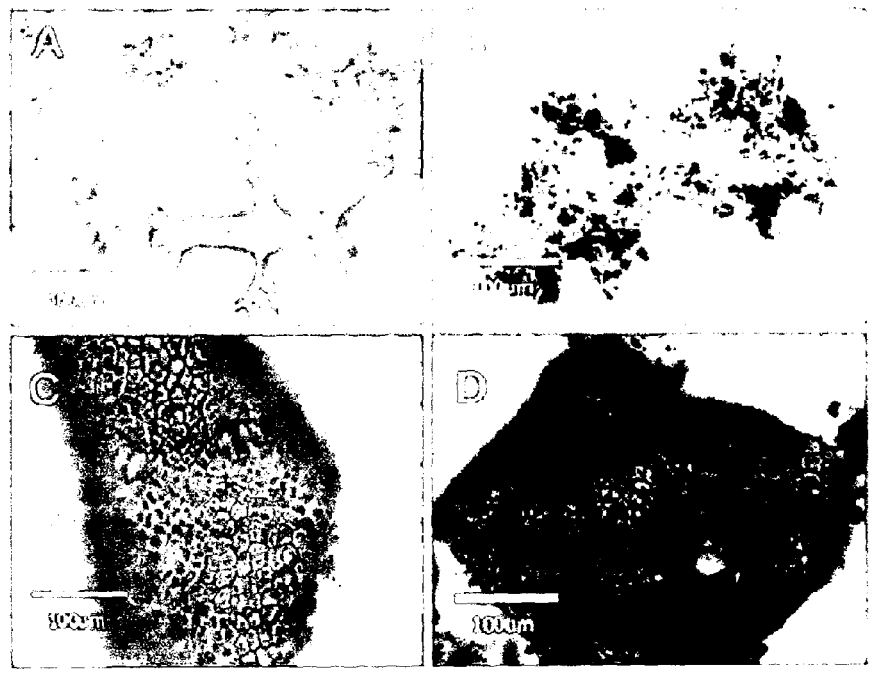

Figure 2

Microscopy 8images of A) fresh orange peel stained with toluidine blue Purple if pectin is present (top left image); B) fraction 1 upon microwave treatment (10mins, 200°C); C) fresh orange peel epidermal tissue treated with CDTA and stained with toluidine blue; D) fraction 1 upon microwave treatment (10mins, 200°C).

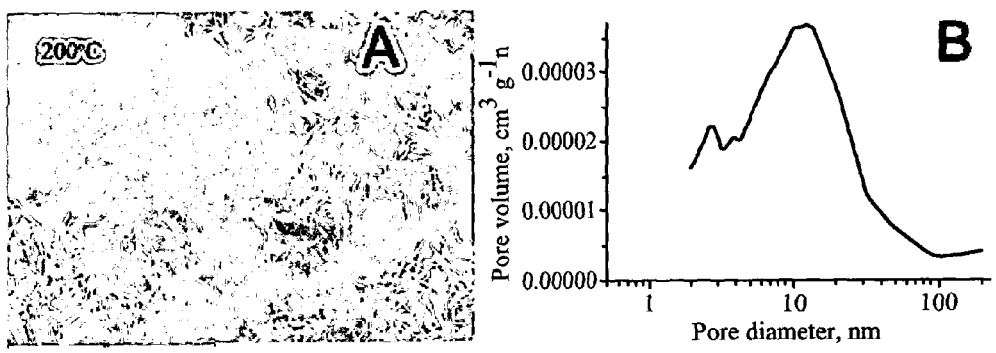

Figure 3

Textural characteristics of solid fraction N1. A) Scanning electron microscope image: B) Pore size distribution obtained from liquid nitrogen adsorption sorption isotherms.

ATR spectrum of solid fraction N1 in comparison with spectrum of pure cellulose (Aldrich).

GC-MS of fraction N2.

ATR spectrum of solid fraction N3 (orange pectin in comparison with spectrum of pure pectin from Aldrich).

DRIFT spectrum of fraction N4.

Textural properties of mesoporous cellulose obtained at different temperature (fraction N1)

GC-MS Spectra bio-oil obtained at temperature 180 and 200° C.

GC-MS spectra bio-oil obtained from lemon at temperature 200°C.

Detailed pectin extraction process.

ESI spectrum of precipitate obtained during the hexane evaporation step to obtain the limonene fraction.

ESI spectrum of the acetone soxhlet extract from microwave mediated steam distilled orange peel.

GC-EI Spectrum of the acetone soxhlet extract from microwave mediated steam distilled orange peel.

ATR-IR spectra of commercial pectin and orange peel extracted pectin (as described in experiment).

Quantitative $^{13}$C NMR of CEM MARS6 hydrothermally extracted pectin from orange peel / low microwave power density of 35WL$^{-1}$ Quantitative $^{13}$C NMR of CEM Discovery hydrothermally extracted pectin from orange peel / high microwave power density of 800WL$^{-1}$ ATR-IR spectra of commercial pectin and orange peel extracted pectin (as described in experiment 9.2. (process b: CEM Discovery 800W/L$^{-1}$)).

Overview of the integrated orange waste biorefinery scheme and its different product streams.

MICROWAVE ASSISTED CITRUS WASTE BIOREFINERY

CROSS REFERENCE TO RELATED APPLICATIONS

This application is the National Stage of International Application No. PCT/GB2013/000154, filed Apr. 4, 2013, which claims priority to United Kingdom Application No. GB 1206034.9, filed Apr. 4, 2012, the contents of both of which are incorporated herein by reference in their entirety.

FIELD OF THE INVENTION

This invention relates to a novel type of biorefinery of citrus waste based on microwave assisted hydrothermal low temperature treatment of citrus processing waste; and to products obtained therefrom.

More particularly, the invention relates the certain organic compounds, such as pectin, D-limonene and flavonoids, which may be isolated from microwave assisted hydrothermal low temperature treatment of citrus waste material.

BACKGROUND OF THE INVENTION

Food waste is generated at a phenomenal scale around the world. The rate at which this waste accumulates and its putrescible and polluting nature represents a problem from economic, social and environmental standpoints.[1] Waste treatment is highly regulated and leads to significant costs. Transformation of waste into high value-added products allows companies to reduce treatment costs, generate additional profits and thus improves their competitiveness. Moreover, the recovery and valorisation process of by-products is part of existing sustainable development and environmental protection requirements.[2]

Fruit and vegetable wastes are produced mainly as the result of processing.[3] Citrus processing waste (CPW) represents a highly relevant feedstock with a great potential in the development of a resource focused biorefinery. CPW is the solid by-product predominantly obtained after juicing operations.[4] Citrus are the largest fruit crop in the world with 94.8 million tonnes grown in 2005.[5] They include mainly: oranges, lemons, limes, grapefruits and tangerines. The largest citrus producing countries, accounting for more than 70% of the world's supply, include the USA, Brazil, China, India, Japan, Spain, Italy, Egypt, South Africa, Turkey and Morocco, with Brazil leading the world in citrus production.[5] As part of the citrus market, processing for juice and other products is very important. Over a quarter of the total citrus production in 2005 has been processed.[6] Processing creates a large amount of waste by-product in the form of peel, seeds, rag (the membranes between the citrus segments) and pulp (juice sacs), representing ca. 50-60% of the whole fruit being discarded after juicing for example.[6] Orange juice production generates waste on a multi tonne scale worldwide: Florida state produces an estimated 5 million tonnes of CPW every year.[7] The Mediterranean region produces 20% of the total citrus fruit production, with Spain being the main producer.[8]

Citrus waste presents major environmental problems as its high carbohydrate content is highly fermentable.[1] Major components of wet CPW are water (80%), soluble monosaccharides, cellulose and hemi-cellulose, pectin, limonene, flavonoids and proteins.[9] CPW can be processed to remove and evaporate the free liquid, dried and be sold as cattle feed, since the waste peel provide filler and a protein source. But with a protein content of only 6%, it is not a high protein source.[10]

Drying CPW (to 10% moisture) is very energy-intensive and costly due to the high water content[7] and using CPW as cattle feed is only marginally profitable.

In recent years, valorisation of CPW has received increasing interest due to the wide variety of interesting compounds it contains. D-limonene (3.78% of dry weight of CPW)[11,12] is an attractive starting compound for industrially relevant fine chemicals and flavour compounds (with identical carbon skeletons, such as carveol, carvone, α-terpineol, perrillyl alcohol and perillic acid).[1] D-limonene can be extracted from citrus peels by steam distillation, extracting over 90% of the limonene this way.[13] Steam diffusion techniques using a steam generator (i.e. using extra water and extra energy to remove this water) result in 1.54% yield (w/w) of essential oil from fresh orange peel, and process time can be reduced to one quarter with the use of microwave irradiation.[14] Ultrasonic methods have also been used for peel treatment increasing yield of essential oils.[15]

Another valuable component of CPW is pectin. Pectin, a complex structural hetero polysaccharide found in non-woody plant tissues, is an important food additive mainly used as a gelling agent and a thickener. It is also used in skincare cosmetics and as drug substrate for colonic drugs. Wet or dry citrus fruits contain roughly 20-30% extractable pectin.[16] The current extraction process is based on acidic hydrolysis of citrus (or apple peel) using a dilute mineral acid (nitric, sulphuric or hydrochloric acid) between 50 and 100° C. and at pH 2-3 for several hours to solubilise the protopectin. Pectin is recovered by precipitation with isopropanol. Common yields of pectin are ~3% of the peel weight.[17] Enzymatic methods have also been studied for pectin extraction, avoiding the reduction of the degree of polymerisation linked with uncontrollable acid hydrolysis conditions.[18]

CPW has other applications, such as a source of fibre, flavonoids from the peel (used in the production of human food and food supplements), as a binding agent in foods, a fermentation substrate for single-cell protein production, and as silage and mosquito repellent.[1] A significant body of literature is available on valorisation strategies for CPW. CPW has been used for pectin extraction by acid hydrolysis and production of activated carbon,[19] pectic enzyme production,[5] dietary fibre extraction,[20] methane production,[21] single-cell protein production,[22] bio-ethanol production by a variety of microorganisms and including simultaneous saccharification and fermentation[4,5,9] and succinic acid production.[13]

However, these applications are limited, especially when considering the volume of CPW and its interesting chemical content.

Nevertheless, there has been little industrial uptake yet and no integrated use of CPW close to the major sources of production, apart from efforts to provide a process for the recovery of a wide variety of products (monosaccharides, essential oils, bio-flavonoids and solid mixture of polysaccharides) suitable for industrial applications. However, in this case the major components of orange peel (cellulose and pectin) have not been separated.[23] Likewise, low grade pectin-cellulose mixture is the major product of another process.[24]

Hydrothermal and microwave processing are known to be effective techniques to break down and extract from bio-waste[25] and specifically for citrus peel.[26] Microwaves are more energy efficient and safer for heating[25,27] and allow the whole medium to be heated simultaneously unlike with conventional heating with which heat is only introduced at the interface of the sample and the heater.[28-30] Microwave processing has been shown to be effective at pilot scale and at large continuous processing scale, for example in waste treatment.[31] The use of microwave irradiation for the conversion of biomass to valuable products has a number of important advantages:

(i) it is mobile;
(ii) it is flexible;
(iii) it reduces $CO_2$ burden;
(iv) it is rapid;
(v) it can be continuous; and
(vi) it has high energy efficiency.

Microwave processing has previously been shown to be effective in the breakdown of citrus peel, enabling extraction of individual phytochemicals like hesperidin, limonene [2,14,32,33] and pectin.[34-36]

A number of reports show that microwave assisted extraction yields pectin of higher quality due to the rapid heating, breaking fewer covalent bonds. [35,37,38] Nevertheless, all these methods use microwave heating as a method of pre-treatment and the pectin is still extracted using acid hydrolysis:

(i) In Kratchanova's work, microwaves were used just as a pre-treating method and the pectin was then extracted by at 80-82° C. with HCl (0.5 M) to lower the pH to 1.5.[40];
(ii) Zhongdong et al. uses the microwaves as a heating method for the extraction of pectin at pH 2 with HCl (85° C. for 4 minutes, 2450 MHz, 1000 W)[36]; and
(iii) Fishman et al. extracts pectin from the albedo of oranges using HCl as a solvent (albedo:solvent 1:25).[39,40,37]

The production of pectin is especially resource demanding and wasteful since it produces large quantities of acidic wastewater.

However, a microwave assisted citrus peel biorefinery, which processes major components of CWP (pectin, cellulose, limonene, monosaccharides, etc.) all together and minimises waste, and without pre-treatment or added acid, has not yet been developed.

SUMMARY OF THE INVENTION

Herein, we describe a novel cascade-type valorisation approach for CPW for the conversion and separation into bio-derived chemicals and materials using low temperature hydrothermal microwave treatment.

We have developed a microwave biorefinery for orange peel whereby in a single process step we separate the limonene from the pectin (useful as a food and cosmetic additive), monosaccharides and cellulose. Two additional interesting features of the process and taking advantage of the important process variables referred to earlier, are that the limonene can be converted in situ into other chemicals by altering the temperature, and that the cellulose produced at certain temperatures is mesoporous (giving it possible value as an adsorbent for example). The overall biorefinery scheme is shown in FIG. 1. A further feature of the process of the present invention is that no extra water is required for microwave assisted steam distillation, for example of limonene.
Process The present invention provides a novel method for the isolation of various components from citrus material. Thus, according to a first aspect of the present invention there is provided a method of isolating one or more of pectin, d-limonene, a flavour compound, a flavonoid, a (soluble) monosaccharide, a decomposition product of a monosaccharide and cellulose, from citrus material wherein said method comprises the microwave assisted hydrothermal low temperature treatment of citrus material.

The citrus material may be combined with water and an organic solvent separately, simultaneously or sequentially. However, it is preferred that the citrus material is combined with water and subjected to microwave as hereinbefore described and the resulting mixture is extracted with an organic solvent.

It will be understood by the person skilled in the art that the term "citrus material" shall include citrus waste material in general, such as citrus peel or waste citrus fruits. However, although it may not be economically beneficial, it is within the scope of the present invention to include any citrus fruits. Citrus material shall include, but shall not be limited to those materials derived from, inter alia, oranges, grapefruits, kumquats, pomelos, tangelos, citrange, citron, lemons, limes, mandarins, tangerines, and the like.

The method of hydrothermal processing of the present invention is widely applicable and is especially suited to use in conjunction with wet waste streams, thus avoiding the necessity to dry waste citrus material prior to the hydrothermal processing.

An important element of this aspect of the invention is that the isolation of the components can be conducted in a substantially acid free environment.

The method of the invention may be carried out at a variety of temperatures, for example room temperature, elevated temperature, etc. The temperature of the extraction process may vary depending upon, inter alia, the choice of organic solvent, etc. Thus, the temperature may vary from room temperature to the boiling point of the water or organic solvent. The mixture of citrus material, water and an organic solvent may be heated during the microwave processing. Where additional heating is necessary, the mixture may be heated to a temperature of from about 80 to about 250° C., preferably from about 90 to about 240° C., preferably from about 100 to about 230° C., preferably from about 110 to about 225° C., preferably from about 120 to about 220° C., for example at about 120° C., 150° C., 180° C., 200° C. or 220° C.

A variety of organic solvents may be used in the method of the invention. The solvent may be polar or non-polar and may be water-miscible or water immiscible. Solvents which may be mentioned include non-polar solvents, such as, ethyl acetate, methyl ethyl ketone, acetone, hexane, methyl isobutyl ketone and toluene. Polar solvents which may be mentioned include lower alcohols such as methanol, ethanol, propanol, isopropanol, or butanol.

The solids-to-solvent ratio may vary and may be from no solvent to about 5:1 w/w, or about 0.1:1 to about 5:1 w/w, or from about 0.2:1 to about 4.5:1 w/w, or from about 0.3:1 to about 4:1 w/w, or from about 0.4:1 to about 3.5:1 w/w, or from about 0.5:1 to about 3:1 w/w, or from about 1:1 to about 2.5:1 w/w, or about 2:1 w/w. These solids-to-solvent ratios are especially suitable for isolation of pectin.

Microwave irradiation is defined as "electromagnetic irradiation in the frequency range of 0.3 to 300 GHz". Specialised chemistry microwave reactors operate at 2.45 GHz and 915 MHz. The microwave irradiation power may vary and may be from about 100 W to about 10 MW (MegaWatts), e.g. 6 kW.
Pectin In one particular aspect of the present invention there is provided a method which comprises the isolation of pectin, from citrus material, wherein said method comprises the microwave assisted hydrothermal low temperature treatment of citrus material.

According to this aspect of the invention, there is further provided pectin isolated by a method as hereinbefore described.

The pectin isolated according to the invention comprises a novel form of pectin. Therefore, the present invention further provides a novel form of pectin. Pectin is a structural heteropolysaccharide contained in the primary cell walls of plants. Although there are several distinct polysaccharides present in pectin, the main component of pectin is D-galacturonic acid. Pectin is used in food as a gelling agent and in medicines, sweets. It is also used as a stabiliser in fruit juices and drinks. Pectin is usually prepared from apple peel or from citrus peel by extracting the peel at pH 1.5-3.0 and 60-100° C., the pectin is precipitated by the addition of isopropanol.

The degree of esterification (DE) of a pectin molecule significantly affects its commercial use as a gelling and thickening agent. Normal pectin, i.e. pectin isolated by conventional methods, has a DE of about 50%. Pectins with a degree of esterification of 50% or more are known to form gels at low pH, e.g. pH 4 or in the presence of sugar.

However, we have found that the form of pectin isolated from the microwave assisted hydrothermal low temperature treatment of citrus processing waste does not gel in a conventional gelation test.

It has been observed that the method of the present invention may produce pectins that gel or, by working at low temperatures or adjusting the microwave power density, pectins that only give thin gels may be produced.

The gelling properties of the isolated pectin may depend upon the microwave power density and the temperature of extraction. For example, pectin susceptible to gelling can be observed when isolated in the presence of a high microwave power density and a temperature of about 120-140° C.

Pectin isolated from a low microwave power density hydrothermal extraction form a standing gel in the presence of acetone. Thus, the invention further provides pectin in the form of a pectin-acetone-water gel.

Thus, the process of the present invention may produce a pectin that forms a very strong, stable gel. It is postulated that the difference between producing a pectin that forms a stable gel and a pectin that forms a thin gel may be related to the sugar content of the pectin, i.e. the sugar content stays high at low temperatures and this may affect the inter and intramolecular interactions that control gelation.

The pectin formed by the microwave assisted hydrothermal low temperature treatment of citrus processing waste according to the present invention has a DE of 80% or more. Thus, the pectin may have a DE of ≥80%, or ≥82%, or ≥85%, or ≥87%, or ≥90%, or ≥92%, or ≥95%, or ≥97%, or ≥99%.

Pectin prepared by the conventional method, e.g. extracting the peel at pH 1.5-3.0 as hereinbefore described, will usually comprises some residual acid. However, it is a further feature of this aspect of the present invention that the pectin prepared by the by the microwave assisted hydrothermal low temperature treatment of citrus material is substantially acid free.

The pectin according to this aspect of the present invention is also advantageous in that it has a low polydispersity, i.e. it has a low molecular weight distribution. Furthermore, pectin according to the present invention generally has a higher molecular weight than commercially available pectins (see Table 6 herein). Thus, the pectin produced by the present invention may have a molecular weight of about $\geq 1 \times 10^5$ g/mol, or about $\geq 1.5 \times 10^5$ g/mol, or about $\geq 2 \times 10^5$ g/mol, or about $\geq 2.1 \times 10^5$ g/mol or about $\geq 2.2 \times 10^5$ g/mol.

Polydispersity is calculated as the Molecular Weight (MW) divided by the number average molecular weight (Mn). Polydispersity data (MW/Mn) is a reference for commercially available pectins. Thus, the pectin according to the present invention may have a polydispersity of from about 1 to about 2.5, from about 1.1 to about 2.4, from about 1.2 to about 2.3, from about 1.3 to about 2.2, from about 1.4 to about 2.1, from about 1.45 to about 2.0, from about 1.5 to about 1.9, from about 1.55 to about 1.8, from about 1.6 to about 1.7.

Thus, according to this aspect of the invention there is also provided a method of preparing pectin with a DE of ≥80% which comprises the microwave assisted hydrothermal low temperature treatment of citrus material. The degree of esterification of may be estimated by, inter alia, quantitative $^{13}$C NMR spectroscopy.

The components of the bio-oil produced will generally comprise the d-limonene, flavour compounds as defined herein, (e.g. terpenes), flavonoids, monosaccharides and other products, depending upon process conditions, including decomposition products of monosaccharides, such as, 5-hydroxymethylfurfural.

Limonene

The present invention also provides a novel method of isolating limonene, more particularly d-limonene from citrus material. Limonene is 1-methyl-4-(1-methylethenyl)-cyclohexene and is usually isolated by the distillation of a cold pressed oil produced as a by-product of orange juice production. Dry citrus peel waste contains about 3.8% d-limonene (w/w), a molecule known for its applications as a bio-solvent, a starting material for synthetic resins, a flavour and fragrance component and a chemical intermediate. D-Limonene is available commercially in an untreated technical grade (purity 95%) and as a food grade (purity 97%) and is usually produced by the steam extraction of dried citrus waste.

Thus, according to a further aspect of the present invention there is provided a method of isolating or extracting d-limonene from citrus material which comprises exposing a mixture of citrus material, water and an organic solvent to microwave energy.

A particular advantage of the method of isolating or extracting d-limonene from citrus material of the present invention is that it is not necessary to add extra water for microwave steam distillation. A high quality limonene can be produced directly from original citrus peel waste, e.g. using internal water. Thus, the present invention especially provides a method of isolating or extracting d-limonene from citrus material which comprises the microwave steam distillation of citrus material in the absence of additional water, i.e. using only internal water from the citrus material.

As hereinbefore described, the current commercial process for the extraction of d-limonene is a two stage process, i.e. cold pressing the citrus peel followed by steam distillation of the oil produced. The method of this aspect of the present invention is advantageous in that, inter alia, d-limonene can be extracted in a single step.

The invention therefore provides limonene and especially d-limonene prepared by the method of the invention, i.e. microwave assisted hydrothermal low temperature treatment of citrus waste material.

Flavour Compounds

In the microwave assisted hydrothermal low temperature treatment of citrus waste material as hereinbefore described, useful flavour compounds, e.g. terpenes, may also be isolated. Thus, for example, certain terpenes which may be mentioned include one or more of trans-carveol, carvol, trans-caryophyllene, citral, copaene, trans-geraniol, d-limonene, linalool, α-myrcene, α-phellandrene, pinene, α-pinene, β-pinene, sabinene, γ-terpinene, δ-terpinene, α-terpinene, α-terpineol, 4-terpineol, valencene and verbenol. Therefore, the present invention further provides one or more terpenes prepared by the method of the invention, i.e. microwave assisted hydrothermal low temperature treatment of citrus waste material, especially those terpenes selected from the group comprising of one or more of trans-carveol, carvol, trans-caryophyllene, citral, copaene, trans-geraniol, d-limonene, linalool, α-myrcene, α-phellandrene, pinene, α-pinene, β-pinene, sabinene, γ-terpinene, δ-terpinene, α-terpinene, α-terpineol, 4-terpineol, valencene and verbenol.

Flavonoids

The method of the invention is also advantageous in that it allows the isolation of flavonoids from citrus material. Since the process of isolation is substantially free from acid, as hereinbefore described, the process is especially suited to the isolation of methoxy flavonoids, i.e. O-methylated flavonoids.

It is understood that direct microwave assisted steam distillation of citrus material removes internal water from the citrus material. Extraction of flavonoids from citrus material may be difficult in the presence of water and therefore the removal of internal water from the citrus material is advantageous in the extraction of flavonoids from citrus material.

Thus, according to a further aspect of the invention there is provided a method of isolating or extracting one or more flavonoids from citrus material which comprises exposing a mixture of citrus material, water and an organic solvent to microwave energy. The invention particularly provides a method of selectively isolating or extracting one or more methoxy flavonoids. Specific methoxy flavonoids which may be mentioned, include, but shall not be limited to, tetra-O-methylscutellarein, tangeritin, nobiletin, hexamethyl-O-myricetin, hepta-methoxyflavone. Other flavonoids which may be mentioned include naringenin, hesperidin, narirutin and rhoifolin. Therefore, the method according to this aspect of the invention especially provides a method of isolating or extracting one or more flavonoids from citrus material which comprises the microwave assisted hydrothermal low temperature treatment of citrus material wherein the flavonoid is selected from the group consisting of tetra-O-methylscutellarein, tangeritin, nobiletin, hexamethyl-O-myricetin, heptamethoxyflavone and naringenin, hesperidin, narirutin and rhoifolin. In a preferred aspect of the invention the isolated flavonoids are methoxylated flavonoids, such as those selected from the group consisting of tetra-O-methylscutellarein, tangeritin, nobiletin, hexamethyl-O-myricetin, heptamethoxyflavone.

Thus, the invention further provides one or more flavonoids, e.g. methoxy flavonoids, prepared by the method of the invention, i.e. microwave assisted hydrothermal low temperature treatment of citrus waste material. Such flavonoids may especially be selected from the group comprising one or more of tetra-O-methylscutellarein, tangeritin, nobiletin, hepta-methoxyflavone and naringenin.

Monosaccharides

The method of the invention is also advantageous in that it allows the isolation of monosaccharides or decomposition products of monosaccharides from citrus material.

Thus, according to a further aspect of the invention there is provided a method of isolating or extracting one or more monosaccharides or the decomposition product of monosaccharides from citrus material which comprises exposing a mixture of citrus material, water and an organic solvent to microwave energy.

Thus, the invention further provides one or more monosaccharides prepared by the method of the invention, i.e. microwave assisted hydrothermal low temperature treatment of citrus waste material. Such monosaccharides may especially be selected from the group comprising one or more of arabinose, fucose, fructose, galactose, rhamnose and xylose. A particular monosaccharide which may be mentioned is fructose. In addition certain decomposition products, such as 5-hydroxymethylfurfural may also be isolated.

Mesoporous Cellulose

The method of the invention also provides a form of mesoporous cellulose as an initial fraction from the microwave hydrothermal pyrolysis of citrus material. Thus, the invention further provides a method for the isolation of a mesoporous cellulose material from citrus material, wherein said method comprises the microwave assisted hydrothermal low temperature treatment of citrus material.

The mesoporous cellulose material has an average pore diameter of from about 5 nm to about 50 nm, from about 7 nm to about 45 nm, from about 9 nm to about 40 nm, from about 10 nm to about 35 nm, from about 12 nm to about 30 nm, from about 14 nm to about 25 nm, from about 16 nm to about 22 nm, from about 18 nm to about 20 nm, e.g. 19 nm.

The pore volume mesoporous cellulose material may be from about $0.1$ $cm^3g^{-1}$ to about $0.8$ $cm^3g^{-1}$, from about $0.2$ $cm^3g^{-1}$ to about $0.7$ $cm^3g^{-1}$, from about $0.25$ $cm^3g^{-1}$ to about $0.6$ $cm^3g^{-1}$, from about $0.3$ $cm^3g^{-1}$ to about $0.5$ $cm^3g^{-1}$, from about $0.35$ $cm^3g^{-1}$ to about $0.4$ $cm^3g^{-1}$, egg $0.38$ $cm^3g^{-1}$.

It will be understood by the person skilled in the art that the isolation of pectin, d-limonene, flavour compounds, flavonoids, soluble monosaccharides (and derivatives of monosaccharides, i.e. decomposition products of monosaccharides, such as 5-hydroxymethylfurfural) and cellulose, from citrus material may be carried out simultaneously. Thus, the present invention further provides for an integrated biorefinery approach to the isolation of the components hereinbefore described from citrus material, e.g. citrus processing waste, based on microwave processing and the simultaneous production of the range of useful products hereinbefore described, e.g. one or more of pectin, d-limonene, a flavour compound, a flavonoid, a soluble monosaccharide and cellulose.

Thus, according to a yet further aspect of the invention there is provided a biorefinery for isolating components from citrus material including the microwave assisted hydrothermal low temperature treatment of the citrus material. Such components include, but shall not e limited to one or more of pectin, d-limonene, a flavour compound, a flavonoid, a soluble monosaccharide and cellulose.

Such a biorefinery is illustrated in FIG. 9 herein. Thus, the biorefinery process may comprise the steps of:

(i) introducing wet citrus material;
(ii) subjecting the citrus material to microwave assisted steam distillation;
(iii) isolating d-limonene, leaving a first citrus material residue;
(iv) subjecting the first citrus material residue to an organic solvent extraction;
(v) isolating flavour compounds, flavonoids and/or monosaccharides, leaving a second citrus material residue;
(vi) subjecting the second citrus material residue to a hydrothermal microwave treatment; and
(vii) isolating pectin and mesoporous cellulose.

The invention will now be illustrated by way of example only and with reference to the accompanying drawing is which:

FIG. 1 is a schematic representation of the processing of orange peel by microwave hydrothermal pyrolysis;

FIGS. 2A) to D) are microscopy images of orange peel before and after microwave treatment;

FIG. 3 A) is a microscopy image of the textural characteristics of solid fraction Mesoporous cellulose;

FIG. 3 B) is a representation of the pore size distribution Mesoporous cellulose obtained from liquid nitrogen adsorption sorption isotherms;

EXAMPLES

Example 1

1.1 Microwave Hydrothermal Treatment of Orange Peel

Waste orange peels (WOP) were sampled from Cordoba (Spain). Prior to their hydrothermal treatment, both peel (containing mostly the organic compounds) and pith (containing mainly polysaccharides) were separated from the rest of the waste oranges, and cut into small pieces (typically 1-2 mm long) to facilitate their processing.

Figure 1:
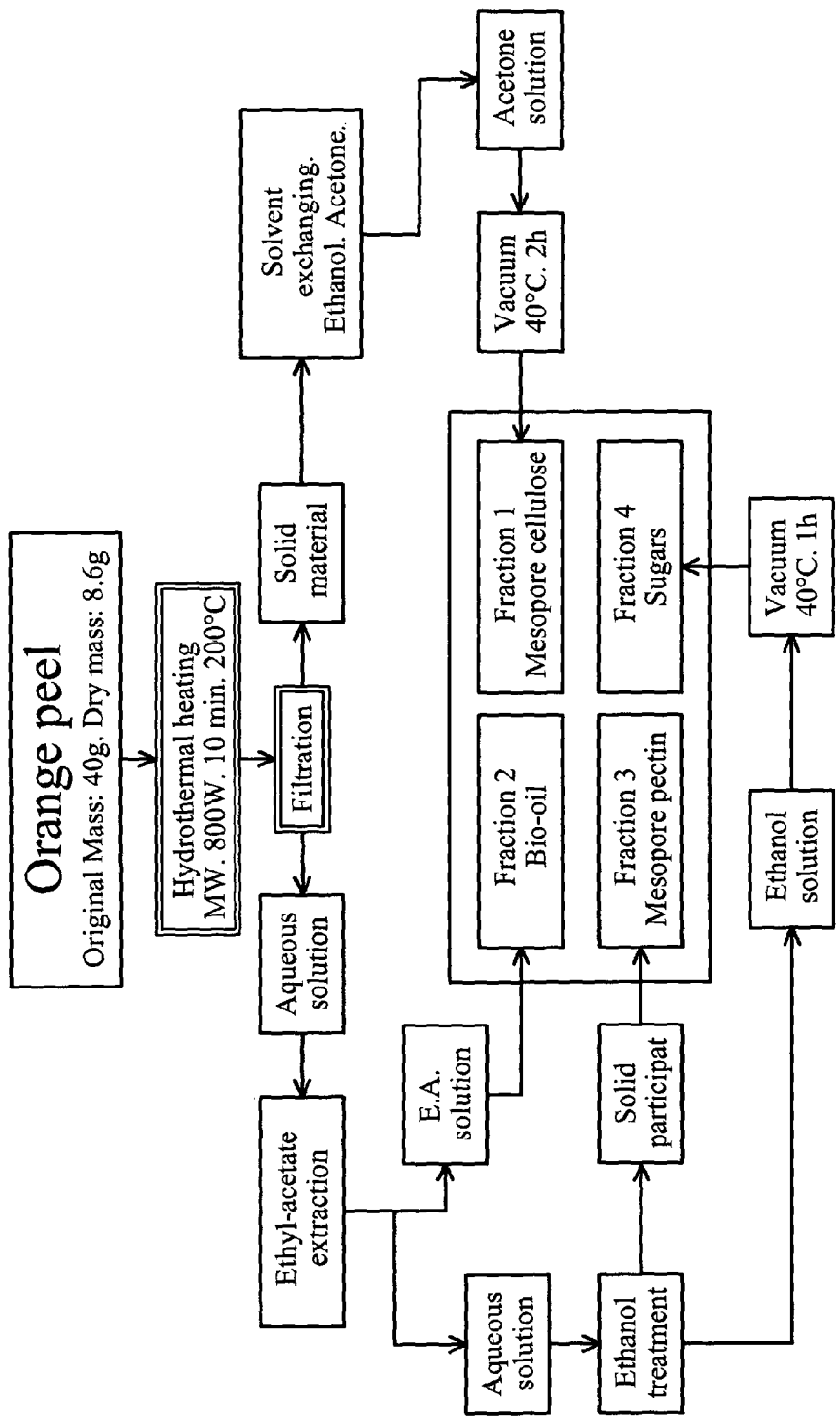

In a typical experiment, 40 g WOP were placed in a Teflon® vial containing 10-20 mL water and subsequently microwaved at a temperature of 200° C. for 10 minutes under continuous stirring. As a result of microwave hydrothermal pyrolysis of orange peel followed by separation steps, four fractions were obtained (see FIG. 1).

1.2 Separation and Characterisation of Fraction N1 (Mesoporous Cellulose)

On the first separation step slurry obtained from orange peel after microwave treatment was filtered off to separate gel from the aqueous solution. Results from the microscopy of the solids remaining after pyrolysis are depicted in FIG. 2. These show that the cells imaged are virtually devoid of pectin, with evidence of increasing black carbonaceous materials accumulated within the cells at longer times of microwave irradiation (FIG. 2A) and B)). Remarkably, much of the cell wall structure is observed to be intact in all cases (FIG. 2C) and D)) and it is assumed that the black carbonation is derived from the oil content of the cells.

Figure 4:
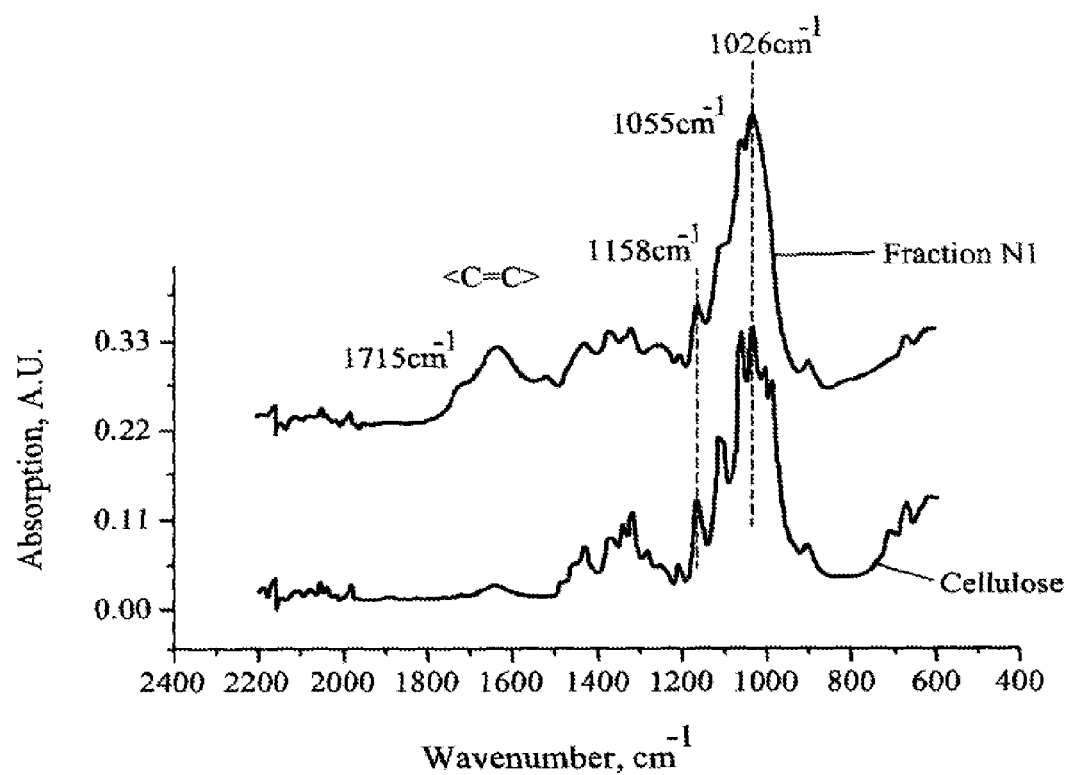
FIG. 4 is an Attenuated Total Reflectance (ATR) FTIR spectrum of Mesoporous cellulose in comparison with a spectrum of pure cellulose.

Microscopy data proves that pectin is completely removed from the cell wall. The gel was then solvent exchanged with ethanol and acetone to remove water from the created meso/macroporous network to prevent its collapse. Drying of the solid after this procedure will result in a solid mesoporous material with average pore diameter around 19 nm and pore volume 0.38 cm$^3$g$^{-1}$ (see FIGS. 3A and 3B). ATR spectra demonstrate the cellulosic nature of these porous materials (see FIG. 4).

1.3 Separation and Characterisation of Fraction N2 (α-Terpineol)

Figure 5:
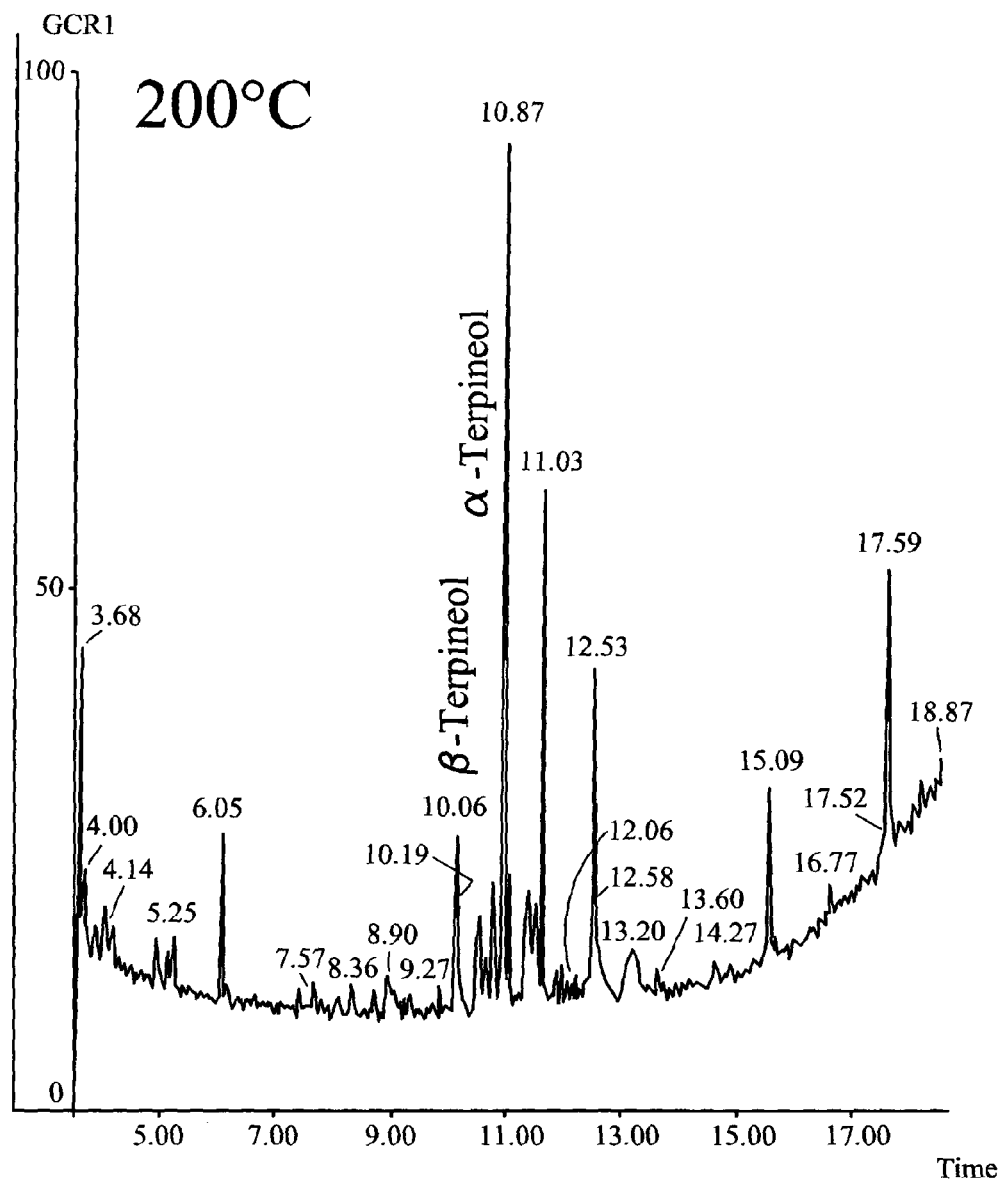
FIG. 5 is a GC-MS of an α-terpineol fraction.

On the second separation step the organic compounds were repeatedly extracted using small volumes (10-20 mL) of ethyl acetate. All extracts were collected and the solvent was removed in a rotary evaporator at 40° C. for 1-2 h. The final organic extract was then analysed and characterised by GC and GC/MS (see FIG. 5).

1.4 Separation and characterisation of fraction N3 (Pectin)

Figure 6:
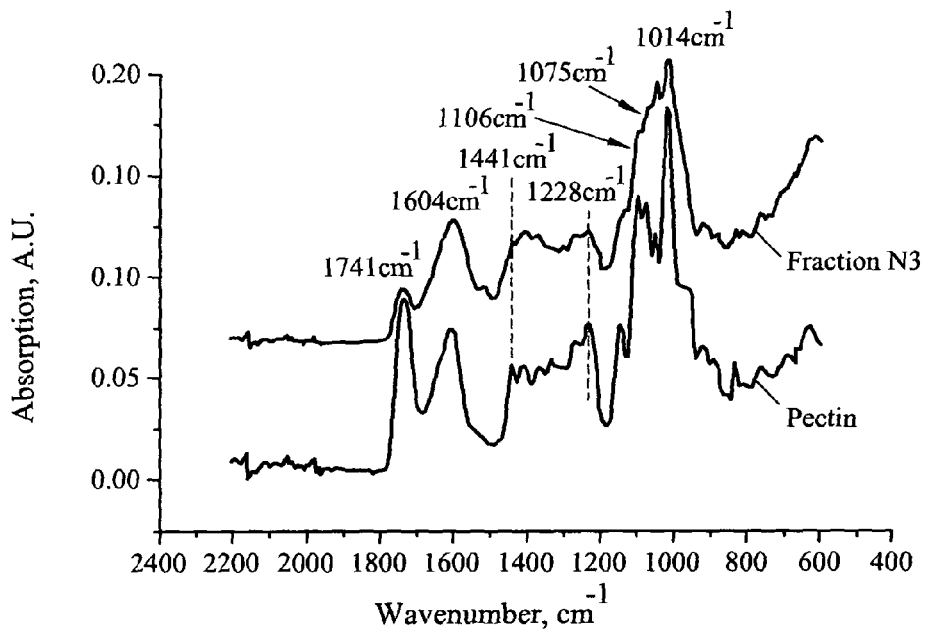
FIG. 6 is an ATR spectrum of a solid pectin fraction N3 (orange pectin in comparison with spectrum of pure pectin)

After α-terpineol extraction the residual aqueous phase was mixed with ethanol in 1:3 ratio (one part of aqueous solution to three parts of ethanol). The resulting solution became cloudy and after 2 h a white material precipitated. The mixture was filtered off to separate the solid material from the water-ethanol solution. The solid material was solvent exchanged with ethanol and then left drying at 40° C. for 12 h to yield a grey solid material. ATR spectrum of this material is in a good agreement with the spectrum of pure pectin obtained from Aldrich (FIG. 6).

1.5 Separation and Characterisation of Fraction N4 (Sugars)

Figure 7:
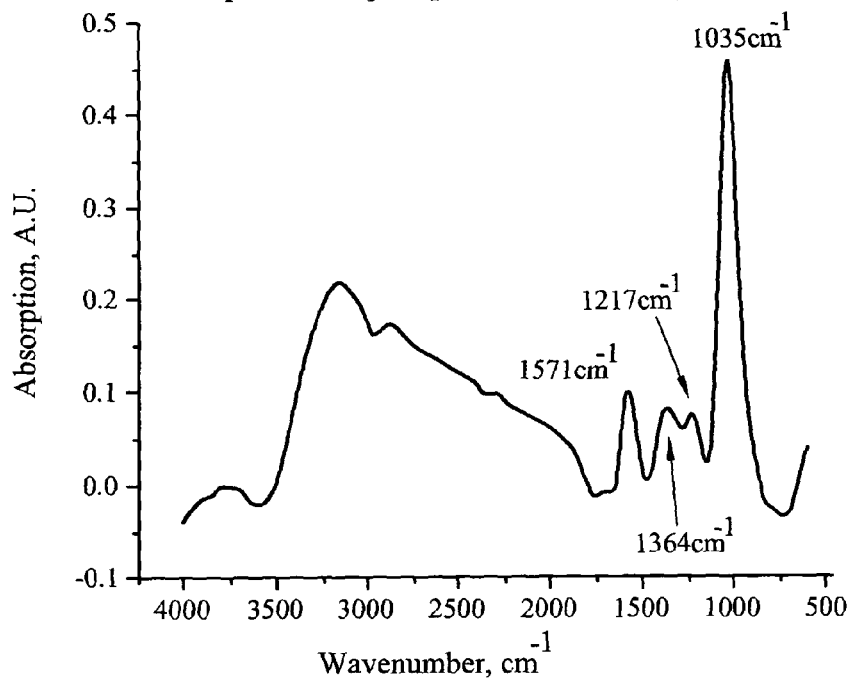
FIG. 7 is a Diffuse Reflectance Infrared Fourier Transform (DRIFT) IR spectrum of a saccharide fraction.

The water-ethanol solution left after pectin separation was dried to yield a solid fraction. FTIR spectra of the solid fraction 4 shows that it is a mixture of sugars (see FIG. 7).

The mass balance of the microwave-assisted hydrothermal treatment of orange peel waste (200° C., 10 minutes) is shown in Table 1.

TABLE 1

Mass balance of the microwave-assisted hydrothermal treatment of orange peel waste (40 g, 200° C.)

| Fractions number | Yield (%) | |
|---|---|---|
| | Based on original weight | Based on dry weight |
| Fraction N1 (porous cellulose) | 3.0 | 11.6 |
| Fraction N2 (bio-oil) | 3.0 | 14.0 |
| Fraction N3 (pectin) | 3.0 | 11.6 |
| Fraction N4 (sugars) | 5.5 | 25.6 |
| Total | 14.5% | 62.8% |

Example 2

Figure 8:
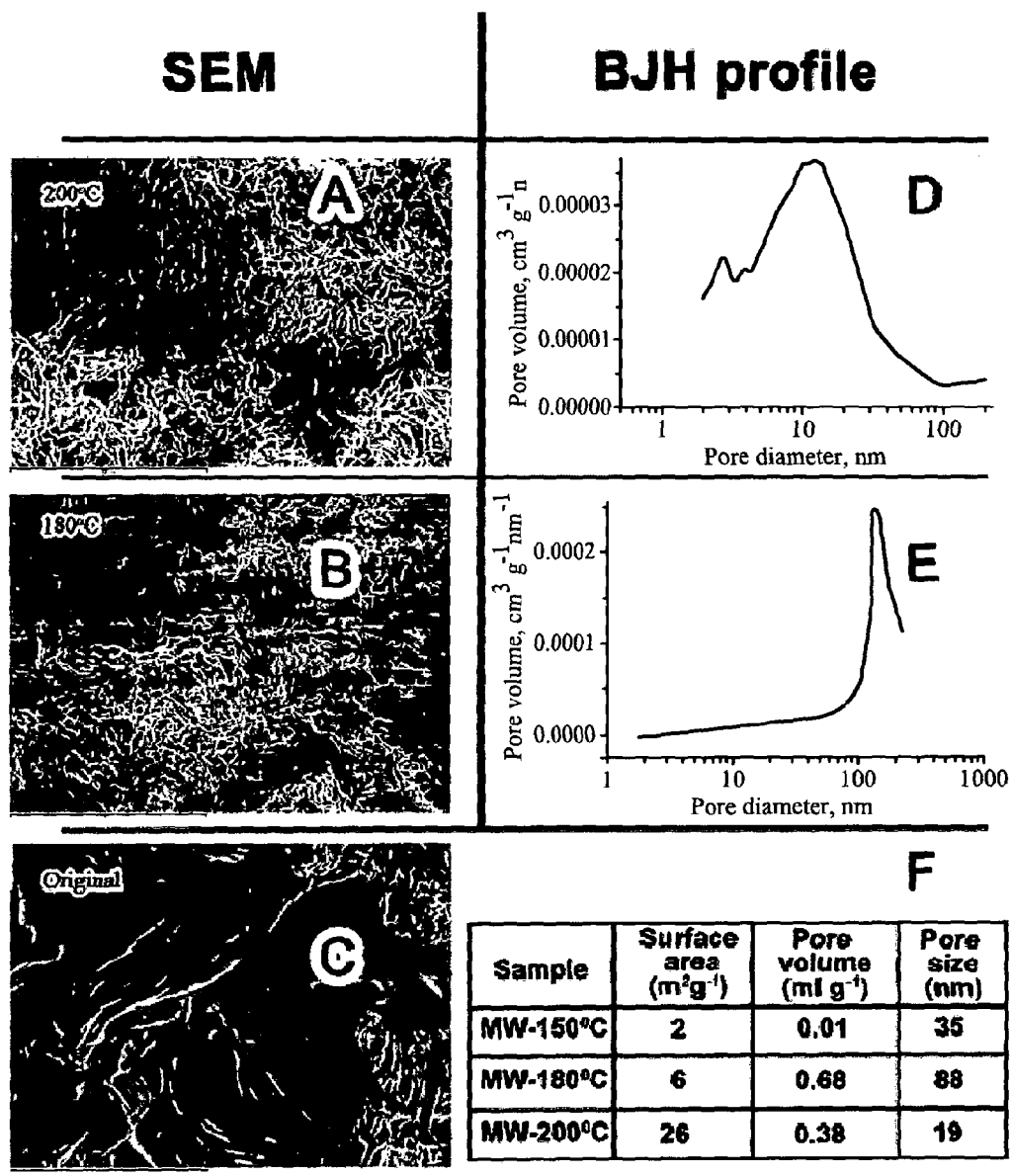
FIG. 8 illustrates the textural properties of mesoporous cellulose obtained at different temperatures.

Influence of the Temperature of the Microwave Hydrothermal Treatment of Orange Peel on the Properties of Mesoporous Cellulose The properties of mesoporous cellulose prepared as for example 1 but at temperature 150, 180 and 200° C. are shown in FIG. 8. The figure demonstrates that the textural properties of the mesoporous cellulose could be controlled by the temperature of the microwave pyrolysis. It was found that cellulose obtained at a temperature of 150° C. was contaminated by pectin.

Example 3

Figure 9:
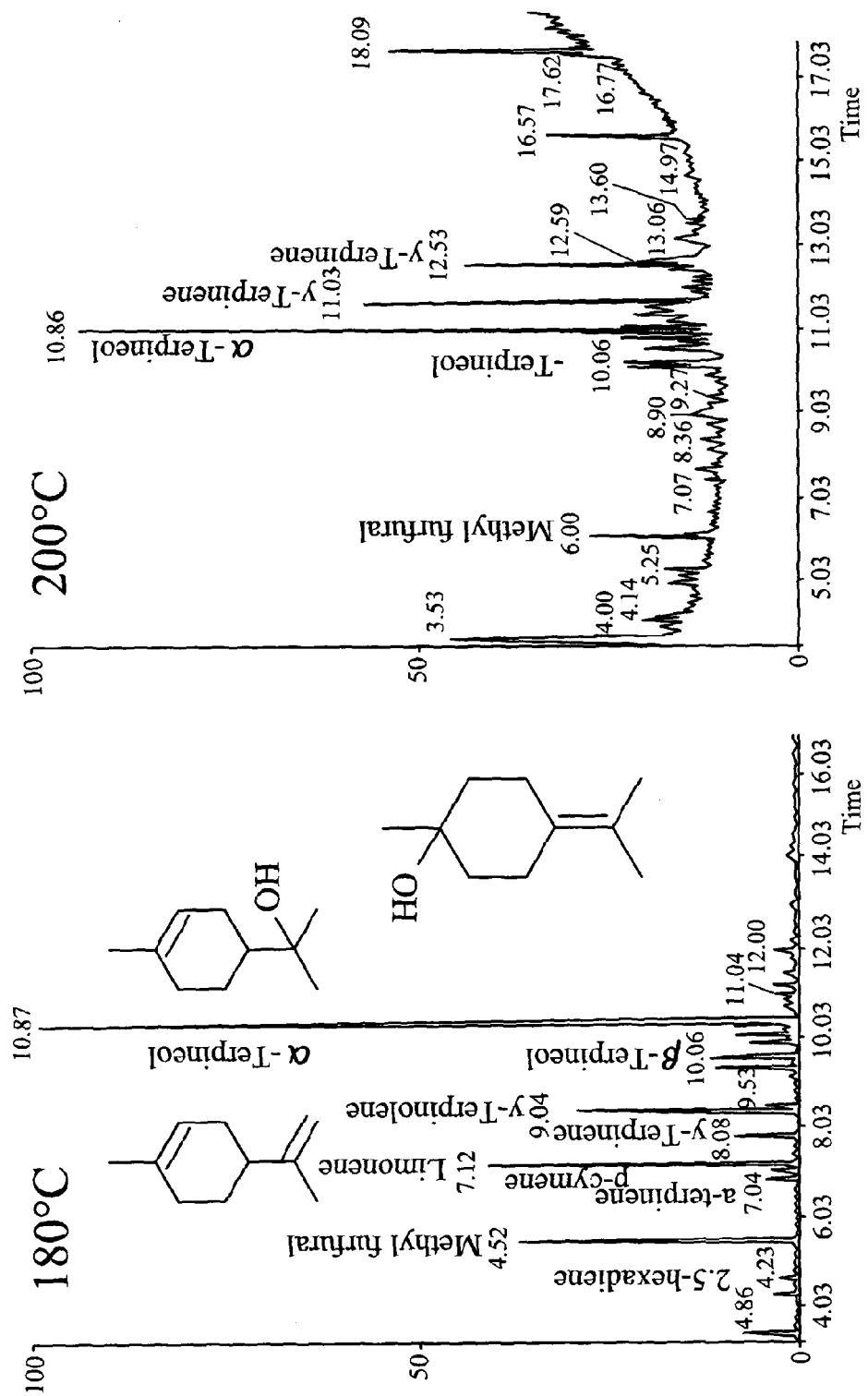
FIG. 9 is a GC-MS spectra of bio-oil obtained at temperatures 180° C. and 200° C.

Influence of the Temperature of the Microwave Hydrothermal Treatment of Orange Peel on the Composition of Bio-Oil The fraction N2 was prepared as for example 1 but at temperature 150, 180, 200 and 220° C. FIG. 9 shows GC-MS spectrum of fractions obtained at 180 and 200° C.

The figure demonstrates that the composition of bio-oil can be controlled by the temperature of the microwave pyrolysis. Influence of the temperature of the hydrothermal microwave pyrolysis on the major component of fraction N2 (bio-oil) is also demonstrated in Table 2.

TABLE 2

Influence of temperature of hydrothermal microwave pyrolysis on the major component of fraction N2 (bio-oil)

| MW pyrolysis temperature (° C.) | Major component of the oil (Based on dry weight) (%) |
|---|---|
| 150 | D-limonene |
| 180 | α-terpineol |
| 200 | α-terpineol |
| 220 | 5-hydroxymethylfurfural |

Example 4

Influence of the Temperature of the Microwave Hydrothermal Treatment of Orange Peel on the Pectin Yield of pectin prepared as for example 1 but at temperature 150° C., 180° C., 200° C. and 220° C. is shown in Table 3.

TABLE 3

Influence of temperature of hydrothermal microwave pyrolysis on the yield of pectin

| MW pyrolysis temperature (° C.) | Pectin yield (%) |
|---|---|
| 150 | 5.70 |
| 180 | 8.70 |
| 200 | 11.6 |
| 220 | 9.70 |

Example 5

Quantitative Determination of Pectin Properties

Determination of pectin's degree of esterification was done following a titration method described in the Food Chemicals Codex[41]. 5 g of pectin was transferred into a beaker, and stirred for 10 min with a mixture of 5 ml of concentrated hydrochloric acid and 100 ml of 60% isopropyl alcohol. The mixture was filtered through a dry, coarse sintered-glass filter tube and washed with six 15-ml portions of the acid-alcohol mixture, followed by 60% isopropyl alcohol until the filtrate was free from chloride. Finally, it was washed with 20 ml of anhydrous isopropyl alcohol, dried at 105° C. for 2.5 hours, cooled and weighed. 500.0 mg of the washed and dried sample was put into 250-ml Erlenmayer flask, and moistened with 2 ml of alcohol. 100 ml of $CO_2$ was added, stopped and swirled occasionally until the sample was completely hydrated. 5 drops of phenolphthalein were added and titrated with 0.1 N sodium hydroxide, recording the volume required as $V_1$ (initial titer) in ml. 200 ml of 0.5 N sodium hydroxide were added, stopped, shaken, and allowed to stand for 15 min. 20.0 ml of 0.5 N HCl were added, shaken until the pink colour disappeared, then 3 drops of phenolphthalein were added, and titrated with 0.1 N sodium hydroxide to a faint pink colour. The volume of 0.1N sodium hydroxide required was recorded as $V_2$ (saponification titer), in ml. The degree of esterification was calculated by the formula $100 \times V_2 / V_1$. It was found for pectin prepared as for example 1 that degree esterification is 93%.

Yield of galacturonic acid has been determined using FTIR analysis.[42] It was found that pectin prepared as for example 1 has a yield of galacturonic acid of 71%.

Example 6

Microwave Hydrothermal Treatment of Lemon Peel

Lemon peel was treated as described in Example 1. It was found that the yield of pectin is 6-7% (based on dry mass). The degree of pectin esterification and the yield of galacturonic acid, measured as described in Example 5 was found to be 45% and 73% respectively.

Figure 10:
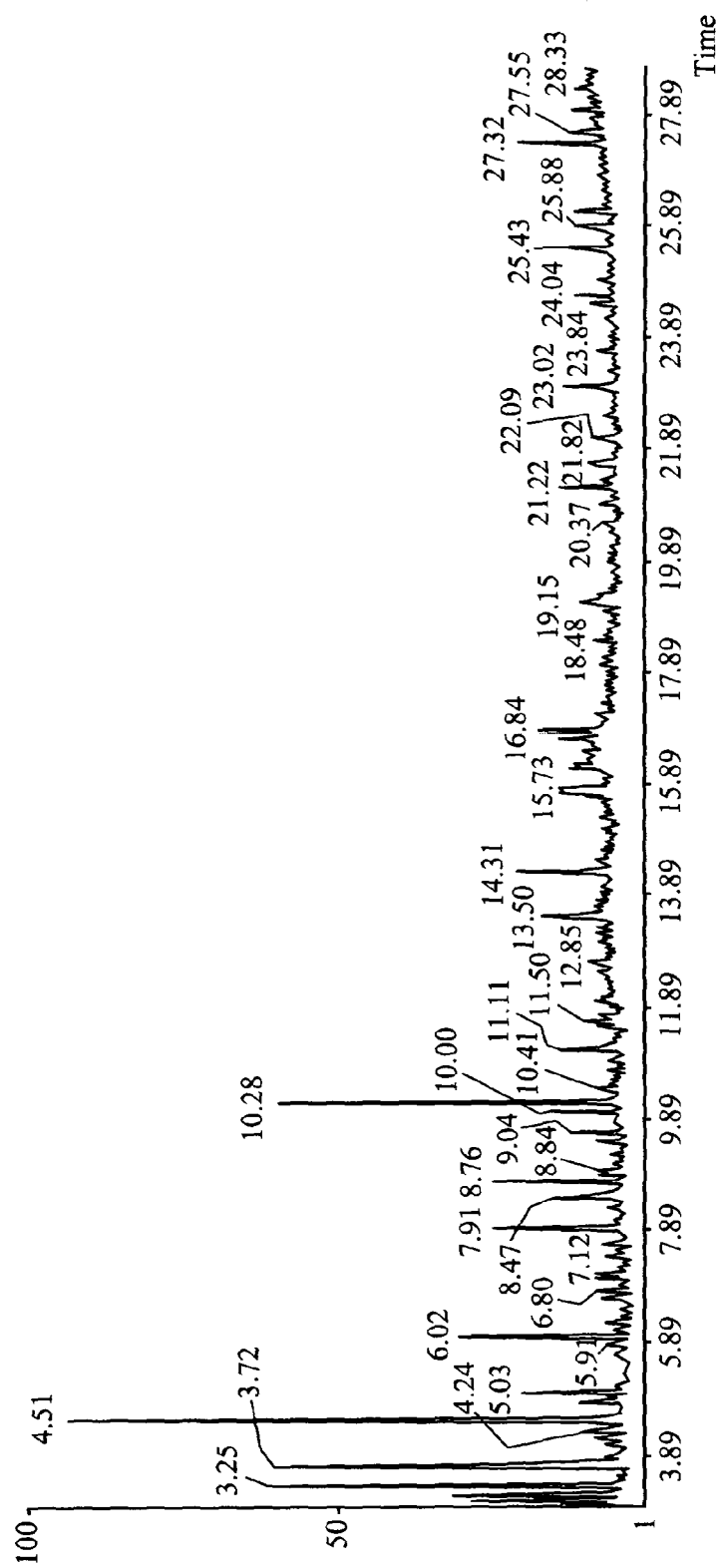
FIG. 10 is a GC-MS spectra bio-oil obtained from lemon at a temperature 200° C.

Result of GC-MS analysis of fraction N2 (bio-oil) is shown in FIG. 10 and Table 4. The major component is a decomposition product of monosaccharides, 5-hydroxymethylfurfural.

TABLE 4

Lemon derived bio-oil composition

| Retention time (mins.) | Compound name |
|---|---|
| 3.35 | methyl pyruvate |
| 3.72 | glyceraldehyde |
| 4.51 | 1,3 dihydroxy-2-propanone |
| 5.03 | 1,2 cyclopentanedione |
| 6.02 | 1,3 hydroxydihydro-2(3H)-furanone |
| 7.91 | pyridinol |
| 8.47 | appears to be a diglyceraldehyde dimer |
| 8.73 | 4H Pyran-4-one, 2,3-dihydro 3,5-dihydroxy, 6-methyl |
| 9.64 | 1,2-benzenediol |
| 10.00 | 3-methylbenzaldehyde |
| 10.15 | 5-hydroxymethylfurfural |
| 14.31 | appears to be levoglucosan |

Figure 11:
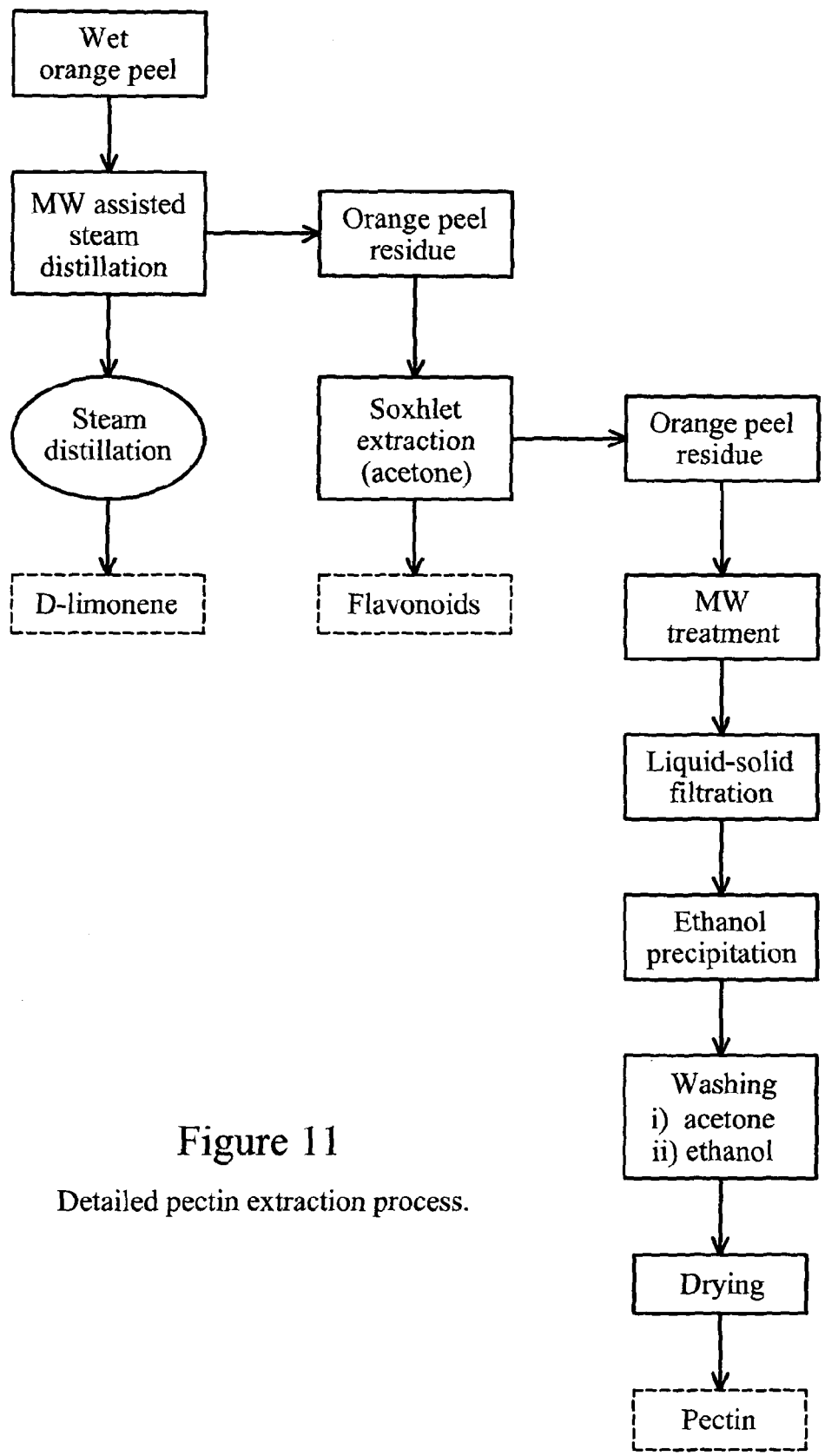
FIG. 11 is a schematic representation of a pectin extraction process.

The sequence of the different experiments of examples 7 to 9 are illustrated in FIG. 11.

Example 7

D-Limonene

Experiment 7.1

Microwave Mediated Hexane Extraction of Limonene from Wet Orange Peel

Microwave heating of wet orange peel in the presence of hexane yielded 1.52% of limonene (dry basis). This experiment was performed in a CEM MARS6 microwave at a 3 L scale using an open vessel fitted with three consecutive water-cooled condensers. The applied microwave power was 1800 W and the total heating/extraction time was 9 min.

The presence of limonene was unequivocally confirmed by $^{13}$C NMR, This spectrum was recorded on a Jeol ECX-400 NMR spectrometer at 100 MHz using the central resonance of CDCl$_3$ (SC=77.16 ppm). $^{13}$C NMR (100 MHz, CDCl$_3$): 20.96; 23.62; 28.07; 30.75; 30.96; 41.24; 108.50; 120.80; 133.89; 150.42.

Experiment 7.2

Microwave-mediated steam distillation of wet orange peel (1200 W for 6 min and then 800 W for 25 minutes, 1 L scale), yielded a maximum of 1.08% limonene (dry basis). GC-MS analysis showed that the essential oil consisted predominantly of limonene (94.83%) with α-myrcene (2.18%), (alpha)-pinene (0.844%), linalool (0.592%) and sabinene (0.265%) as the most important side products. The complete composition is shown in Table 5.

TABLE 5

Composition of the Essential Oil Obtained From the Microwave Mediated Steam Distillation of Wet Orange Peel

| Compound | CAS # | Retention time (s) | Kovats Index | Relative area to Sigma Aldrich D-limonene (%) | Peak ratio (%) |
|---|---|---|---|---|---|
| D-limonene | 138-86-3 | 392.5 | 1028 | 99.540 | 94.829 |
| alpha myrcene | 123-35-3 | 368.8 | 981 | 0.103 | 2.180 |
| *pinene | 2437-95-8 | 362.1 | 969 | 0.011 | 0.844 |
| alpha pinene | 80-56-8 | 342.3 | 931 | | 0.844 |
| linalool | 78-70-6 | 421.0 | 1085 | | 0.592 |
| sabinene | 3387-41-5 | 361.4 | 967 | | 0.265 |
| decanal | 112-31-2 | 469.2 | 1188 | | 0.138 |
| cis limonene oxide | 13837-75-7 | 438.8 | 1122 | 0.119 | |
| beta pinene | 127-91-3 | 364.5 | 973 | | 0.118 |
| delta terpinene | 586-62-9 | 419.8 | 1083 | | 0.103 |
| alpha terpineol | 98-55-5 | 465.7 | 1180 | | 0.090 |
| gamma terpinene | 99-85-4 | 404.5 | 1052 | | 0.074 |
| alpha phellandrene | 99-83-2 | 377.7 | 999 | | 0.068 |
| carvol | 99-49-0 | 486.6 | 1227 | 0.058 | |
| valencene | 4630-07-03 | 598.8 | 1505 | | 0.055 |
| verbenol trans | 473-67-6 | 433.0 | 1110 | 0.049 | |
| limonene oxide | 4959-35-7 | 440.8 | 1127 | 0.035 | 0.011 |
| 4-terpineol | 562-74-3 | 460.8 | 1169 | | 0.034 |
| citronella | 106-23-0 | 445.0 | 1135 | | 0.029 |
| *citral 2 | 106-26-3 | 498.0 | 1253 | | 0.027 |
| Unknown 20 | 460-01-5 | 439.5 | 1124 | 0.026 | |
| *citral 1 | 106-26-3 | 485.5 | 1224 | | 0.023 |
| trans carveol | 1197-07-5 | 477.5 | 1206 | 0.022 | |
| unknown 28 | 29548-13-8 | 470.8 | 1191 | 0.017 | |
| alpha terpinene | 99-86-5 | 384.2 | 1011 | | 0.015 |
| unknown 31 | 2102-62-7 | 482.9 | 1218 | 0.011 | |
| copaene | 3856-25-5 | 554.1 | 1388 | | 0.010 |
| unknown 30 | 1197-06-4 | 482.7 | 1218 | 0.010 | |
| trans caryophyllene | 87-44-5 | 572.0 | 1434 | | 0.010 |
| trans geraniol | 106-24-1 | 482.3 | 1217 | | 0.010 |

Example 8

Flavonoids

Experiment 8.1

Microwave Mediated Hexane Extraction of Flavonoids from Wet Orange Peel

Figure 12:
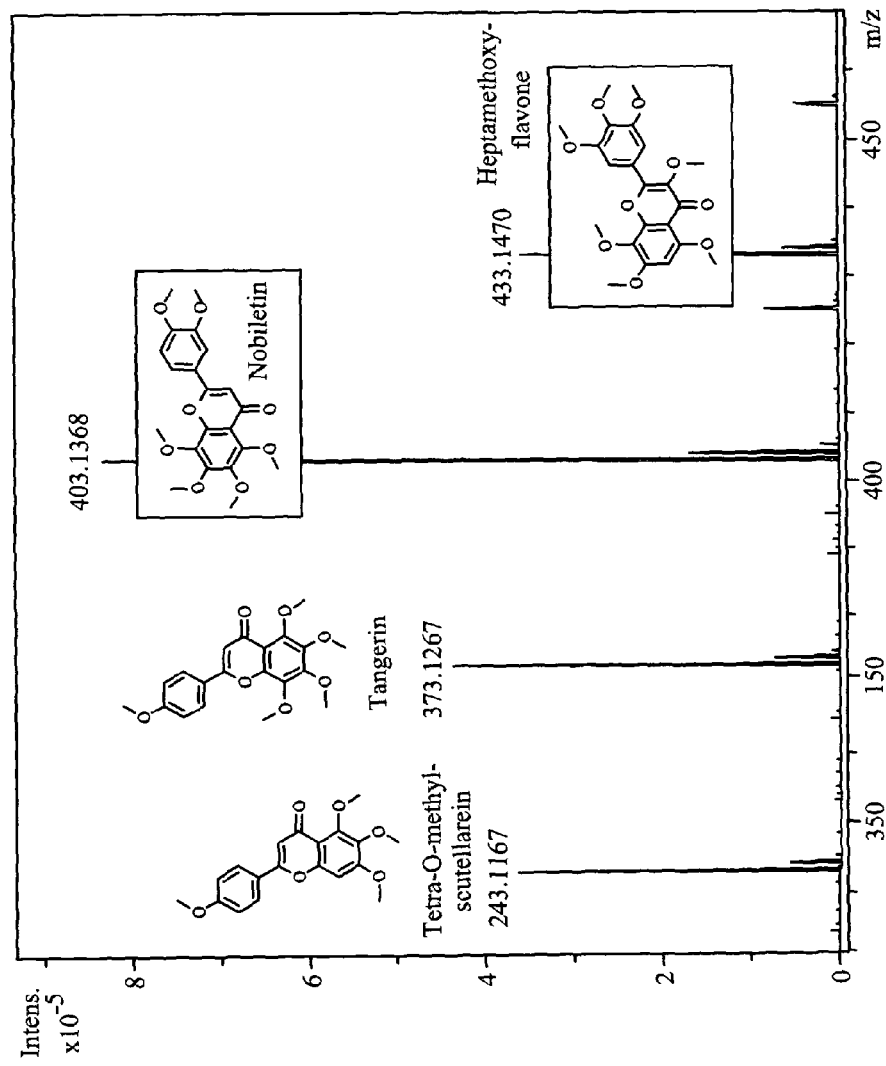
FIG. 12 is an Electrospray Ionisation (ESI) spectrum of flavonoids precipitated during evaporation of hexane fraction from limonene isolation.

Hexane evaporation as to recover the pure limonene in experiment 7.1 yielded a distinct precipitate. The latter was analyzed by ESI mass spectrometry. It was found to consist of 4 different polymethoxyflavones being tetra-O-methylscutellarein, tangeritin, nobiletin and hepta-methoxyflavone. These are of considerable importance as they exhibit a range of interesting medicinal properties such as anti-inflammatory, anti-carcinogenic, anti-atherogenic, anti-diabetic and anti-fungal. Additionally, some polymethoxyflavones have found application as sweeteners or sweetness enhancers. The full ESI spectrum, with the appropriate annotations, is shown in FIG. 12.

Experiment 8.2

Figure 13:
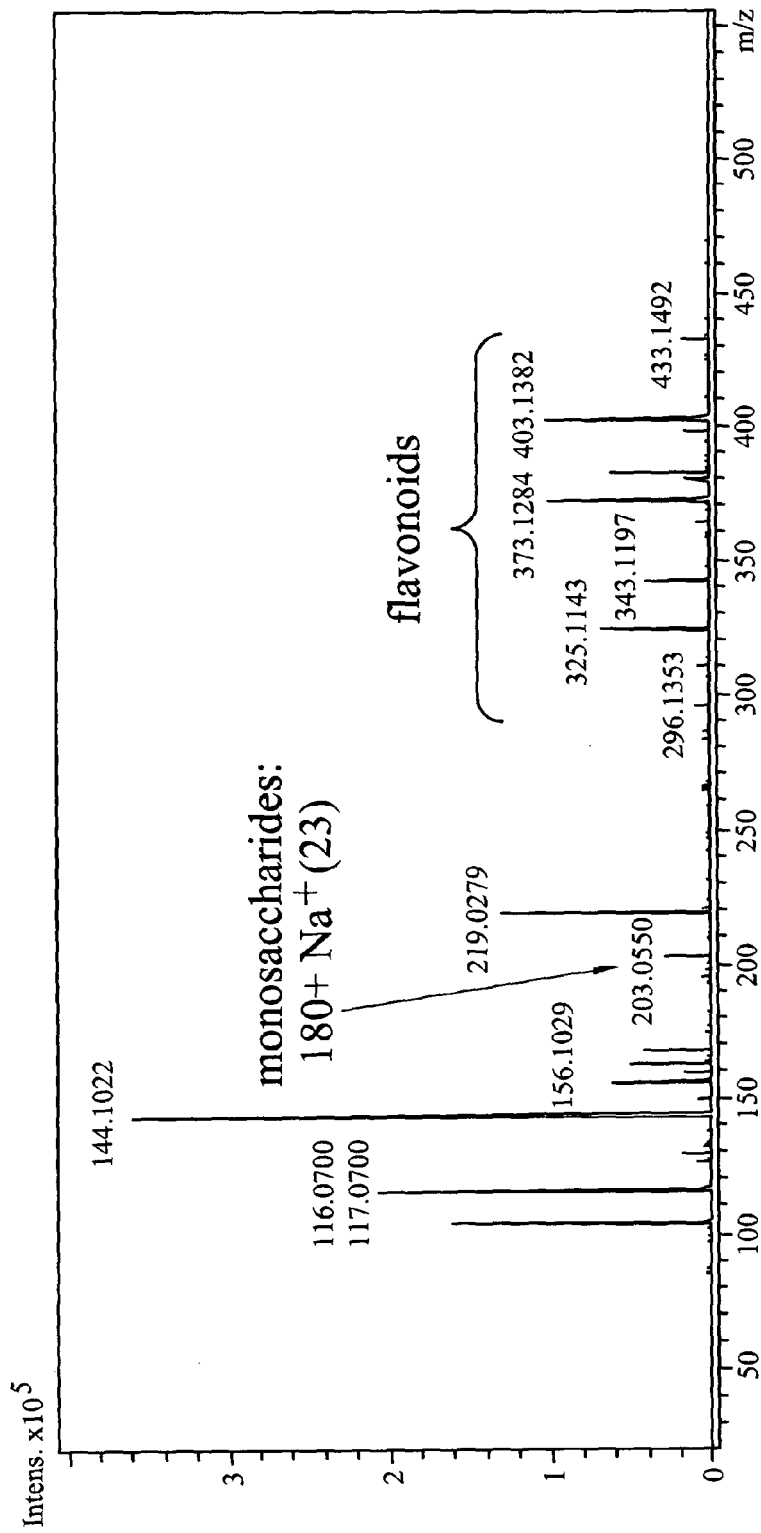
FIG. 13 is an Electrospray Ionisation (ESI) spectrum of an acetone soxhlet extraction from microwave mediated steam distilled orange peel.
Figure 14:
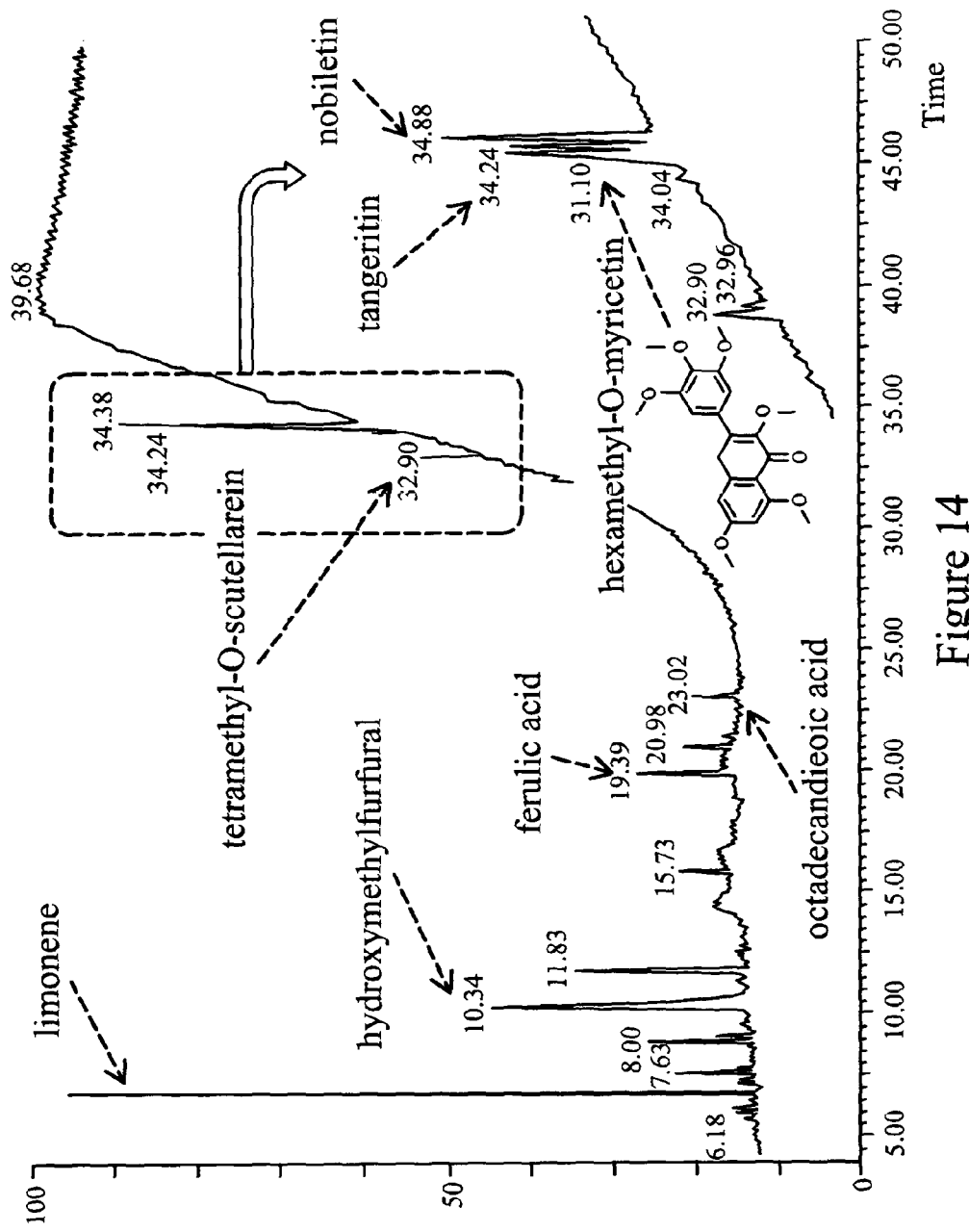
FIG. 14 is a GC-EI spectrum of an acetone soxhlet extract from microwave mediated steam distilled orange peel.

Acetone Soxhlet Extraction of Flavonoids from Microwave Steam Distilled Orange Peel Alternatively, the flavonoids can also be obtained by subjecting steam distilled orange peel (see experiment 7.2) to a subsequent acetone soxhlet extraction. This procedure also removes monosaccharides [ESI spectrum: peak at 203 m/z=180+Na$^+$], residual limonene, hydroxymethylfurfural (HMF), lignin-derived aromatics, fatty acids and any natural acid present. The ESI and GC-EI spectra are shown in FIGS. 13 and 14.

Example 9

Pectin

Microwave Mediated Hydrothermal Extraction of Pectin from Orange Peel

Experiment 9.1

Orange peel subjected to a microwave assisted steam distillation and a subsequent acetone soxhlet extraction, was subjected to a microwave mediated hydrothermal extraction step as to extract the pectin at 120° C. with a low microwave power density of ~35 WL$^{-1}$ (CEM MARS6). The microwave power density is calculated as the total microwave power input divided by the total volume of the microwave cavity. A 9.2% yield of pectin was obtained and this without the use of additional strong acids (e.g. HCl).

Figure 15:
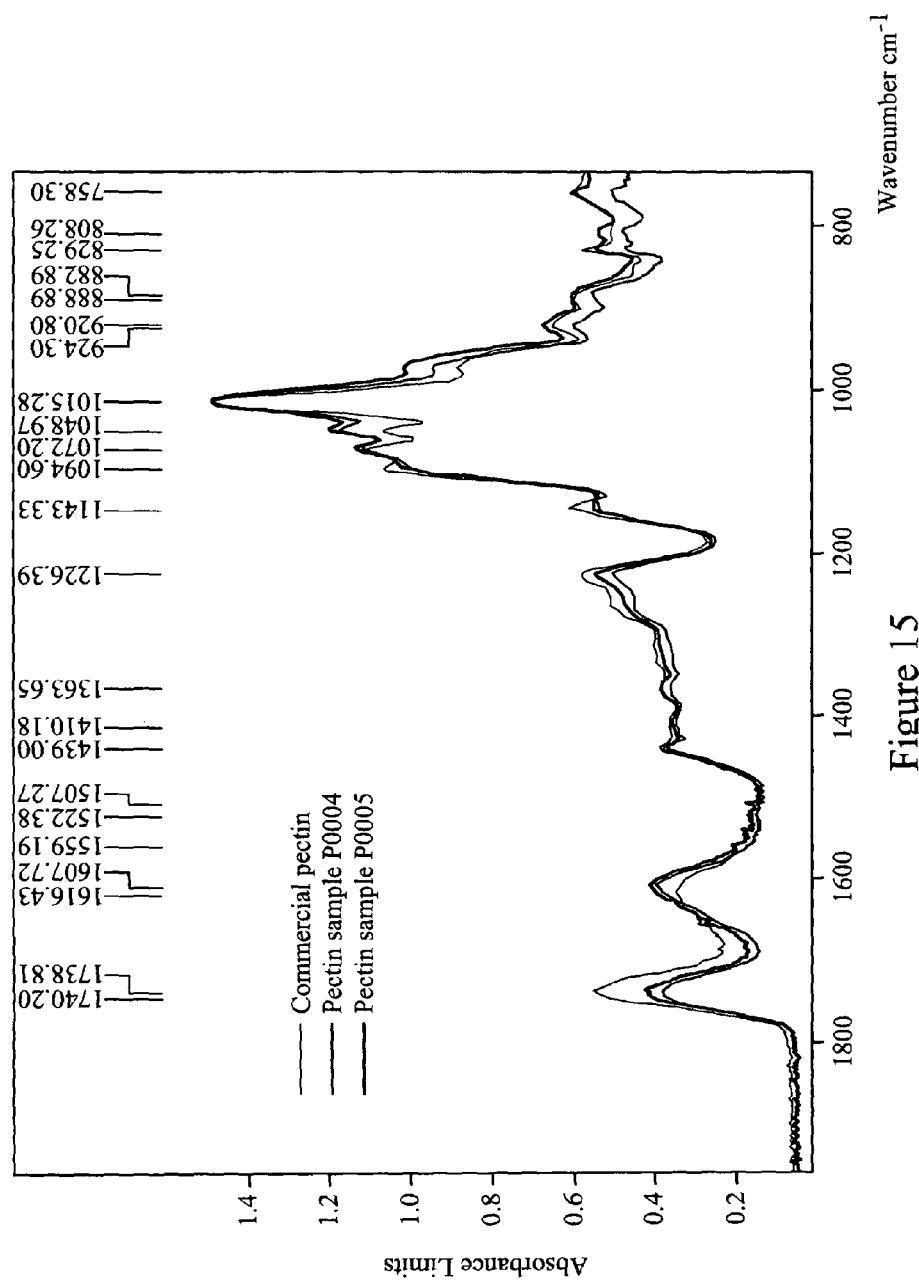
FIG. 15 illustrates ATR-IR spectra of commercial pectin and orange peel extracted pectin (as described in experiment 9.1)

The ATR-IR of this pectin resembles very well the one of commercial pectin (see FIG. 15). Microwave-assisted hydrothermally extracted pectin (MHT pectin), and a commercial reference, were analysed by triple detection gel permeation chromatography. The "MHT pectin" samples were analyzed in duplicate: P0004 and P0005. The latter two show a higher molecular weight (Mw) and number average molecular weight (Mn) and a lower polydispersity (Mw/Mn) than commercial pectin with good reproducibility of the results. The data are summarized in Table 6.

TABLE 6

Molecular weight (Mw) and number average molecular weight (Mn) and polydispersity data (Mw/Mn) for a reference commercial pectin and two microwave mediated hydrothermally extracted pectins

| | Description | Mn (g/mol) | MW (g/mol) | MW/Mn |
|---|---|---|---|---|
| P9135 | Aldrich commercial pectin | $3.15 \times 10^4$ | $8.93 \times 10^4$ | 2.83 |
| P0004 | Microwave extracted pectin | $1.43 \times 10^5$ | $2.29 \times 10^5$ | 1.62 |
| P0005 | Microwave extracted pectin | $1.31 \times 10^5$ | $2.23 \times 10^5$ | 1.71 |

Figure 16:
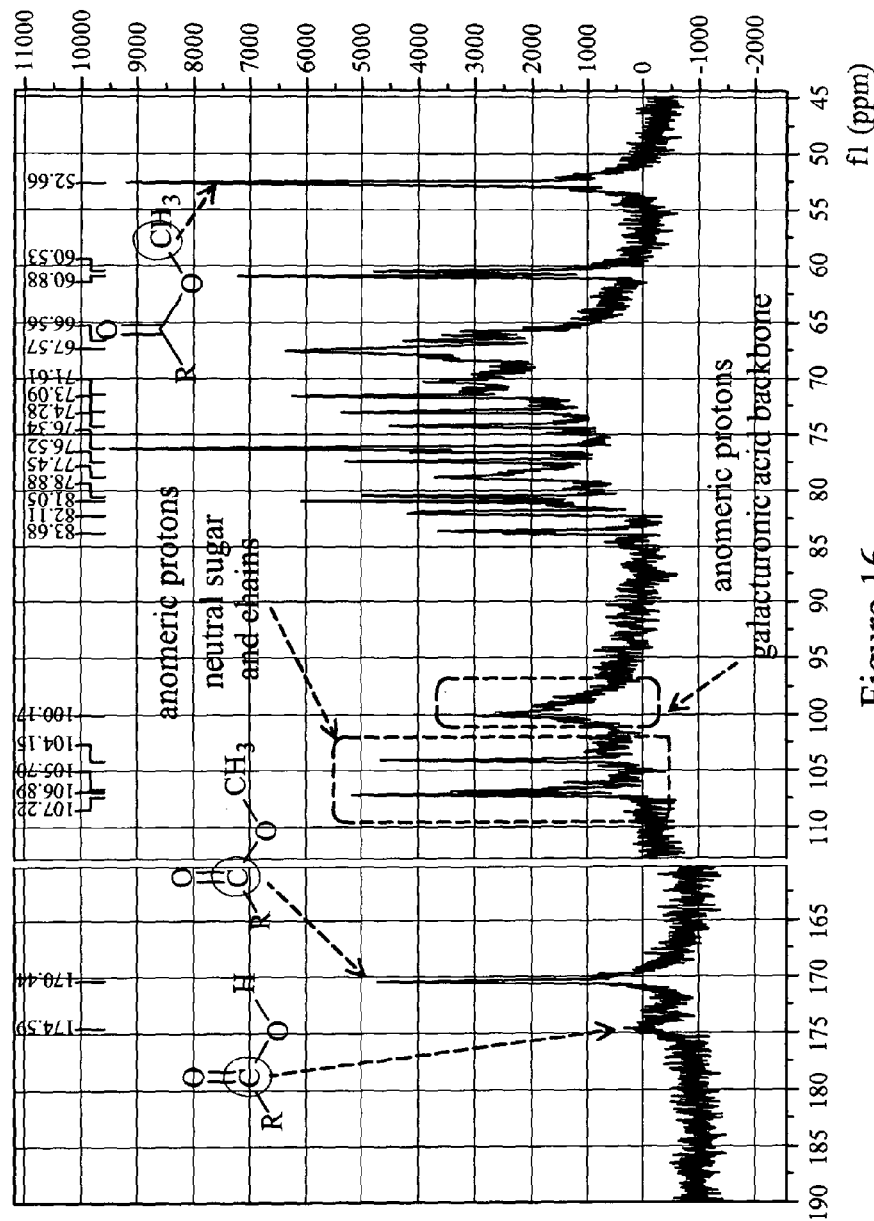
FIG. 16 is a quantitative $^{13}$C NMR of CEM MARS6 (microwave) hydrothermally extracted pectin from orange peel at low microwave power density of 35 WL$^{-1}$.

The degree of esterification of sample P0004 was estimated by quantitative $^{13}$C NMR spectroscopy (see FIG. 16) to be around 80%. This classifies our pectin as a high methoxylated pectin. Note in this respect also the pronounced —CO—O—CH$_3$ peak at ~52.66 ppm underlining further the high esterification degree.

Our data shows that it is possible to extract pectin hydrothermally without the addition of strong acids such as HCl.

Experiment 9.2

Figure 17:
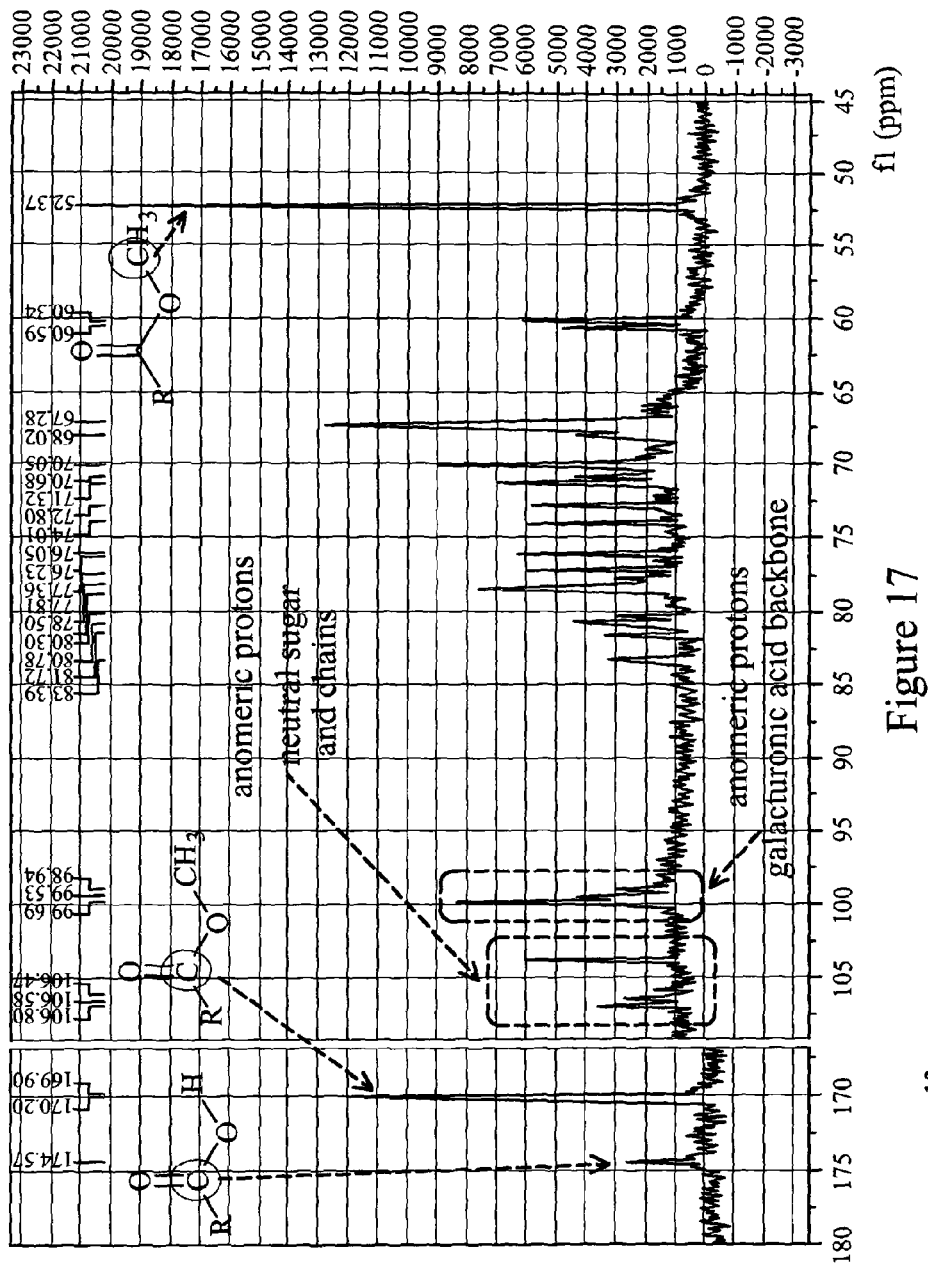
FIG. 17 is a quantitative $^{13}$C NMR of CEM Discovery (microwave) hydrothermally extracted pectin from orange peel at high microwave power density of 800 WL$^{-1}$.

Microwave Mediated Hydrothermal Extraction of Pectin from Orange Peel: An Influence of Microwave Power Density A distinct effect of power density was found in using two different microwave set-ups to effect the pectin extraction from orange peel subjected to both a microwave mediated steam distillation and an acetone soxhlet extraction, with a different microwave power density: a) CEM MARS6: 35 W/L$^{-1}$ and b) CEM Discovery 800 W/L$^{-1}$. All other experimental conditions in this experiment were equal to the ones of experiment 9.1. From quantitative $^{13}$C NMR spectra it was found that the content of neutral sugar side chains in the extracted pectin was markedly lower when a higher power density was used: compare FIGS. 16 and 17.

Figure 18:
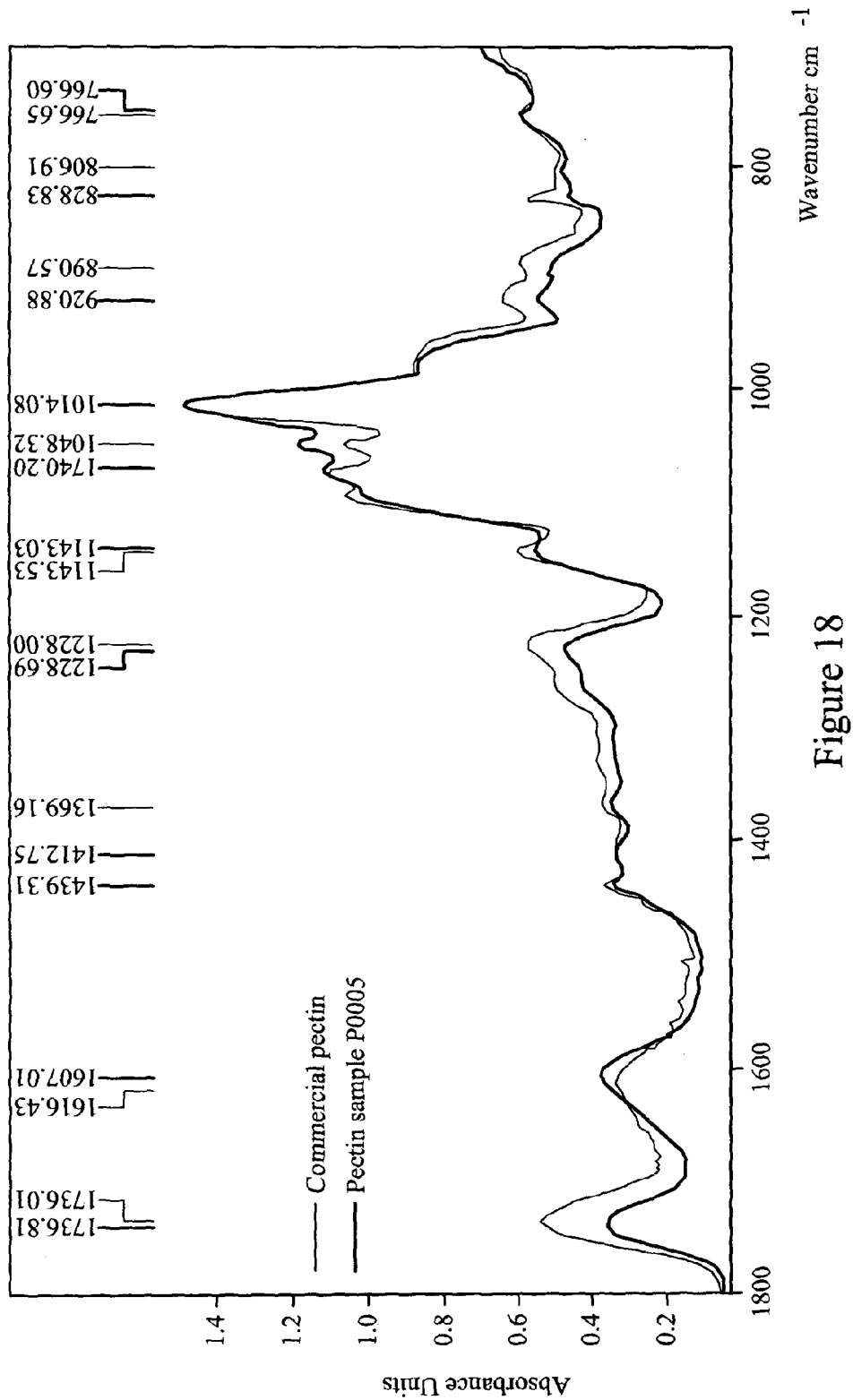
FIG. 18 is an ATR-IR spectra of commercial pectin and orange peel extracted pectin (as described in experiment 9.2 (process b: CEM Discovery 800 W/L$^{-1}$)
Figure 19:
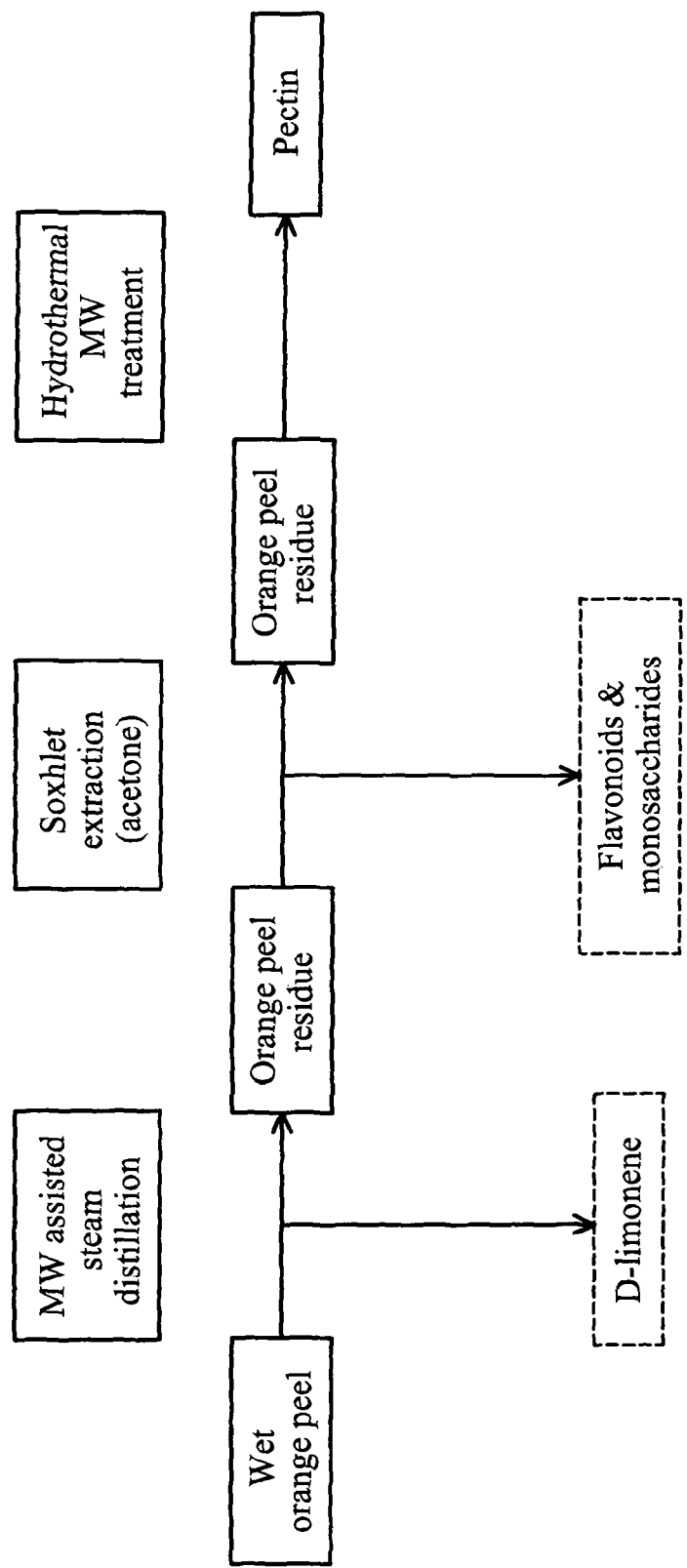
FIG. 19 is a schematic representation of an integrated orange waste biorefinery process and its different product streams.

The degree of esterification of the CEM Discovery extracted pectin was estimated by quantitative $^{13}$C NMR spectroscopy (see FIG. 17) to be around 80%. This classifies this pectin as a high methoxylated pectin. Note in this respect also the pronounced —CO—O—CH$_3$ peak at ~52.37 ppm underlining further the high esterification degree. The ATR-IR of this pectin resembles very well the one of commercial pectin (see FIG. 18).

REFERENCES

1. V. Ferreira-Leitão, L. M. Fortes Gottschalk, M. A. Ferrara, A. Lima Nepomuceno, H. B. Correa Molinari and E. P. S. Bon, *Waste and Biomass Valorization*, 1, 65-76.
2. N. Sahraoui, M. A. Vian, M. El Maataoui, C. Boutekedjiret and F. Chemat, *Innovation in Food Science and Emerging Technologies*, 2011, 12, 163-170.
3. G. T. Kroyer, *Lebensm.-Wiss. u.-Technol.*, 1995, 28, 547-552.
4. W. Widmer, W. Zhou and K. Grohmann, *Bioresource Technology*, 2010, 101, 5242-5249.
5. J. A. Siles Lopez, Q. Li and I. P. Thompson, *Critical Reviews in Biotechnology*, 2010, 30, 63-69.
6. P. Singh nee'Nigam and A. Pandey, eds., *Biotechnology for Agro-Industrial Residues Utilisation*, Springer, 2009.
7. K. Bevill, Freshly squeezed ethanol, Accessed 23.09.11, 2011.
8. Anonymous, *Citrus clementina*, http://www.cns.fr/spip/Citrus-clementina-Mediterranean.html, Accessed 20.10.2011, 2011.
9. W. Zhou, W. Widmer and K. Grohmann, *Proceedings State Florida Horticulture Society*, 2008, 121, 307-310.
10. R. A. Jones, Citrus peel processing system and method, 2006, U.S. Pat. No. 7,060,313 B2.
11. V. A. Bampidis and P. H. Robinson, *Animal Feed Science and Technology*, 2006, 128, 175-217.
12. R. J. Braddock, *Handbook of Citrus By-Products and Processing Technology*, Wiley-Interscience, 1999.
13. Q. Li, J. A. Siles and I. A. Thompson, *Applied microbiological biotechnology*, 2010, 88, 671-678.
14. A. Farhat, A. S. Fabiano-Tixier, M. El Maataoui, J. F. Maingonnat, M. Romdhane and F. Chemat, *Food Chemistry*, 2011, 125, 255-261.
15. A. Patist, T. T. Mindaye and T. Matthiesen, *Process and apparatus for enhancing peel oil extraction*, 2005, US 2006/0204624 A1.
16. A. Steinbüchel and S. K. Rhee, *Polysaccharides and Polyamides in the Food Industry: Properties, Production, and Patents*, Wiley-VCH, 2005.
17. D. A. Kimball, *Citrus Processing, A Complete Guide*, Aspen Publication, 1999.
18. J. A. Donaghy and A. M. McKay, *Bioresource technology*, 1994, 47, 25-28.
19. E. Ma, Q. Cervera and G. M. M. Sanchez, *Bioresource technology*, 1993, 44, 61-63.
20. F. R. Marin, C. Soler-Rivas, O. Benavente-Garcia, J. Castillo and J. A. Perez-Alvarez, *Food chemistry*, 2007, 100, 736-741.
21. P. Ozmen and S. Aslanzadeh, Master of Science, University of Boras, 2009.
22. K. L. Kalra, H. S. Grewal and S. S. Kahlon, *MIRCEN Journal*, 1989, 5, 321-326.
23. J. M. Bonnell, Process for the production of useful products from orange peel, 1985, U.S. Pat. No. 4,497,838.
24. M. L. Fishman and H. K. Chau, Extraction of pectin by microwave heating under pressure, 2000, U.S. Pat. No. 6,143,337.
25. V. L. Budarin, P. S. Shuttleworth, J. R. Dodson, A. J. Hunt, B. Lanigan, R. Marriott, K. J. Milkowski, A. J. Wilson, S. W. Breeden, J. Fan, E. H. K. Sin and J. H. Clark, *Energy & Environmental Science*, 2011, 4, 471-479.
26. R. J. White, V. L. Budarin and J. H. Clark, *European Journal of Chemistry*, 2010, 16, 1326-1335.
27. M. J. Gronnow, R. J. White, J. H. Clark and D. J. Macquarrie, *Organic Process Research & Development*, 2005, 9, 516-518.

28. C. O. Kappe, *Angewandte Chemie International Edition*, 2004, 43, 6250-6284.
29. A. De la Hoz, A. Diaz-Ortiz and A. Moreno, *Chemical Society Review*, 2005, 34, 164-178.
30. F. Yu, S. Deng, P. Chen, Y. Liu, Y. Wan, A. Olson, D. Kittelson and R. Ruan, *Applied Biochemistry and Biotechnology*, 2007, 137, 950-957,
31. D. E. Clark and W. H. Sutton, *Annual Review of Materials Science*, 1996, 26, 299-331.
32. Y. Liu, J. Shi and T. A. G. Langrish, *Chemical Engineering Journal*, 2006, 120, 203-209.
33. M. Ferhat, B. Meklati, J. Smadja and F. Chemat, *Journal of Chromatography A*, 2006, 1112, 121-126.
34. M. L. Fishman and H. K. Chau, *Extraction of pectin by microwave heating under pressure*, 2000, U.S. Pat. No. 6,143,337.
35. M. Kratchanova, E. Pavlova, I. Panchev and C. Kratchanov, *Pectins and Pectinases*, 1996, 14, 941-946.
36. L. Zhongdong, W. Guohua, G. Yunchang and J. F. Kennedy, *Carbohydrate Polymer*, 2006, 64, 548-552.
37. M. L. Fishman, H. K. Chau, P. D. Hoagland and A. T. Hotchkiss, *Food Hydrocolloids*, 2006, 20, 1170-1177.
38. M. Kratchanova, E. Pavlova and I. Panchev, *Carbohydrate polymers*, 2004, 56, 181-185.
39. M. L. Fishman, H. K. Chau, P. Hoagland and K. Ayyad, *Carbohydrate research*, 2000, 323, 126-138.
40. 2000.
41. N. R. C, U. S. C. o. S. o. t. F. C. Codex, *Food chemicals codex*, National Academies, 1981.
42. A. Kumar and G. S. Chauhan, *Carbohydrate Polymers*, 2010, 82, 454-459.

The invention claimed is:

1. A biorefinery process comprising the steps of:
  (i) introducing wet citrus material;
  (ii) subjecting the citrus material to microwave assisted steam distillation;
  (iii) isolating d-limonene, leaving a first citrus material residue;
  (iv) subjecting the first citrus material residue to an organic solvent extraction;
  (v) isolating flavour compounds, flavonoids, monosaccharides, or combinations thereof, leaving a second citrus material residue;
  (vi) subjecting the second citrus material residue to a hydrothermal microwave treatment;
  (vii) isolating pectin and mesoporous cellulose.

2. A process according to claim 1 wherein the citrus material is citrus peel.

3. A process according to claim 1 wherein the wet citrus material comprises water and an organic solvent.

4. A process according to claim 3 wherein the solids-to-solvent ratio is from about no solvent to about 5:1 w/w.

5. A process according to claim 1 wherein the pectin has DE of $\geq 80\%$.

6. A process according to claim 1 wherein the pectin is substantially acid free.

7. A process according to claim 1 wherein the pectin has a polydispersity of from about 1 to about 2.5.

8. A process according to claim 1 wherein the pectin has a molecular weight of about $\geq 1 \times 10^5$ g/mol.

9. A process according to claim 1 which comprises the isolation of a flavour compound.

10. A process according to claim 1 which comprises the isolation of a flavonoid.

11. A process according to claim 1 which comprises the isolation of a monosaccharide or the decomposition product of a monosaccharide.

12. A process according to claim 1 wherein the hydrothermal microwave treatment is carried out at a temperature of 80 to 250° C.

13. A process according to claim 1 wherein the organic solvent is a non-polar solvent.

14. A process according to claim 1, wherein the organic solvent is selected from the group consisting of ethyl acetate, methyl ethyl ketone, acetone, hexane, methyl isobutyl ketone, toluene, and combinations thereof.

15. A process according to claim 1 wherein the organic solvent is acetone.

16. A process according to claim 1 wherein the microwave irradiation power is from about 100 W to about 10 MW.

17. A process according to claim 1 wherein the mesoporous cellulose material has an average pore diameter of from about 5 nm to about 50 nm.

18. A process according to claim 1 wherein the mesoporous cellulose material has a pore volume of from about 0.1 $cm^3 g^{-1}$ to about 0.8 $cm^3 g^{-1}$.

* * * * *